US009161735B2

(12) United States Patent
Bradford et al.

(10) Patent No.: US 9,161,735 B2
(45) Date of Patent: Oct. 20, 2015

(54) SYSTEMS, COMPOSITIONS, AND METHODS FOR LOCAL IMAGING AND TREATMENT OF PAIN

(75) Inventors: David S. Bradford, Sausalito, CA (US); Jeffrey C. Lotz, San Mateo, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1646 days.

(21) Appl. No.: 12/053,379

(22) Filed: Mar. 21, 2008

(65) Prior Publication Data

US 2009/0030308 A1  Jan. 29, 2009

Related U.S. Application Data

(63) Continuation of application No. PCT/US2006/036943, filed on Sep. 21, 2006.

(60) Provisional application No. 60/719,670, filed on Sep. 21, 2005, provisional application No. 60/750,990, filed on Dec. 15, 2005.

(51) Int. Cl.
*A61B 6/00* (2006.01)
*A61B 5/00* (2006.01)
*A61K 49/00* (2006.01)
*A61N 7/02* (2006.01)

(52) U.S. Cl.
CPC ............... *A61B 6/506* (2013.01); *A61B 5/4041* (2013.01); *A61K 49/0002* (2013.01); *A61B 5/4824* (2013.01); *A61N 7/02* (2013.01)

(58) Field of Classification Search
None
See application file for complete search history.

(56) References Cited

U.S. PATENT DOCUMENTS

| | | | |
|---|---|---|---|
| 5,391,197 A | 2/1995 | Burdette et al. | |
| 5,844,092 A * | 12/1998 | Presta et al. | 530/387.3 |
| 6,074,352 A | 6/2000 | Hynynen et al. | |
| 6,126,682 A | 10/2000 | Sharkey et al. | |
| 6,231,528 B1 | 5/2001 | Kaufman et al. | |
| 6,254,553 B1 * | 7/2001 | Lidgren et al. | 601/3 |
| 6,368,292 B1 | 4/2002 | Ogden et al. | |
| 6,470,220 B1 | 10/2002 | Kraus, Jr. et al. | |
| 6,491,893 B1 | 12/2002 | Babich | |
| 6,562,033 B2 | 5/2003 | Shah et al. | |
| 6,575,969 B1 | 6/2003 | Rittman, III et al. | |
| 6,699,242 B2 | 3/2004 | Heggeness | |
| 6,736,835 B2 | 5/2004 | Pellegrino et al. | |
| 6,827,716 B2 | 12/2004 | Ryan et al. | |
| 6,907,884 B2 | 6/2005 | Pellegrino et al. | |
| 2003/0139652 A1 | 7/2003 | Kang et al. | |
| 2004/0064136 A1 | 4/2004 | Papineau et al. | |
| 2004/0064137 A1 | 4/2004 | Pellegrino et al. | |
| 2004/0120891 A1 * | 6/2004 | Hill et al. | 424/1.41 |

FOREIGN PATENT DOCUMENTS

| | | |
|---|---|---|
| CN | 1326351 A | 12/2001 |
| WO | 00 41514 A2 | 7/2000 |
| WO | 03059437 A2 | 7/2003 |
| WO | 03061756 A2 | 7/2003 |
| WO | 2004022055 A1 | 3/2004 |
| WO | 2004032870 A2 | 4/2004 |
| WO | WO 2004032718 A2 * | 4/2004 |
| WO | 2004058184 A2 | 7/2004 |
| WO | 2004060409 A1 | 7/2004 |
| WO | 2004073653 A2 | 9/2004 |
| WO | 2004096122 A2 | 11/2004 |
| WO | 2005000194 A2 | 1/2005 |
| WO | 2005000283 A2 | 1/2005 |
| WO | 2005011689 A2 | 2/2005 |
| WO | 2005039393 A2 | 5/2005 |
| WO | 2005044178 A2 | 5/2005 |
| WO | 2005048987 A1 | 6/2005 |

OTHER PUBLICATIONS

Loo C, Lowery A, Halas N, West J, Drezek R. Immunotargeted nanoshells for integrated cancer imaging and therapy. 2005 Nano Lett. 5: 709-711. Published online Mar. 22, 2005.*

Kairemo et al. In vivo detection of intervertebral disk injury using a radiolabeled monoclonal antibody against keratan sulfate. 2001 J. Nucl. Med. 42: 476-482.*

Freemont et al. Nerve growth factor expression and innervation of the painful intervertebral disc. 2002 J. Pathol. 197: 286-292.*

Ding et al. In vivo tracking of implanted stem cells using radio-labeled transferrin scintigraphy. 2004 Nucl. Med. Biol. 31: 719-725.*

State Intellectual Property Office of China, Notification of the Third Office Action issued on Sep. 28, 2012 for corresponding Patent Application No. 200680042827.2, English translation (pp. 1-4), claims examined (pp. 5-25) and original Chinese language (pp. 25-29), counterpart to PCT/US2006/036943, claiming priority to U.S. Appl. No. 60/719,670, pp. 1-29.

(Continued)

*Primary Examiner* — Michael G Hartley
*Assistant Examiner* — Jennifer Lamberski
(74) *Attorney, Agent, or Firm* — John P. O'Banion

(57) ABSTRACT

Pain factors are labeled with targeted agents or markers delivered into the body. The labeled pain factors are imaged with appropriate imaging tools in a manner allowing selective identification and localization of areas of pain source or transmission. The labeled pain factors allow spatial differentiation in the imaging sufficient to specify the location of the pain so as to drive therapeutic decisions and techniques in order to treat the pain. Pain factors labeled and imaged in this manner may include one or more of nerve factors, blood vessel factors, cellular factors, and inflammation factors. Labeled markers may include for example radioactive materials (e.g. tritiated or iodinated molecules) or other materials such as metal (e.g. gold) nanoparticles.

31 Claims, 9 Drawing Sheets

(56) References Cited

OTHER PUBLICATIONS

Japanese Patent Office, Decision of Refusal issued on Oct. 30, 2012 for corresponding Japanese Patent Application No. 523410/2008, counterpart to PCT/US2006/036943, English translation (pp. 1-4), claims examined (pp. 5-15) and original Japanese language (pp. 16-18) pp. 1-18.
C-T. Chung et al. Single photon emission computed tomography (SPECT) for low back pain induced by extension with no root sign. J. Chin. Med. Assoc. vol. 67, pp. 349-354 (2004).
J.O. Lusins et al. SPECT and lumbar MRI in back pain with emphasis on changes in end plates in association with disc degeneration (abstract). J. Neuroimaging, vol. 8, No. 2, pp. 78-82 (1998).
M. McDonald et al. Use of computer tomography—single-photon emission computed tomography fusion for diagnosing painful facet arthropathy. Neurosurg. Focus, vol. 22, No. 1, E2 (2007).
D.S. Mulconrey et al. Interobserver reliability in the interpretation of diagnostic lumbar MRI and nuclear imaging. The Spine Journal, vol. 6, pp. 177-184 (2006).
State Intellectual Property Office of China, Notification of the First Office Action, related Chinese Patent Application No. 200680042827.2, issued Nov. 12, 2010, including claims examined, pp. 1-19.
Japanese Patent Office, Notice of Reasons for Refusal issued on Jan. 17, 2012, corresponding Patent Application No. 2008-532410, English translation (pp. 1-6), original Japanese language (pp. 7-11), with claims examined (pp. 12-22), counterpart to PCT/US2006/036943, claiming priority to U.S. Appl. No. 60/719,670, pp. 1-22.
State Intellectual Property Office of China, Notification of the Second Office Action issued on Jan. 31, 2012, corresponding Patent Application No. 200680042827.2, English translation (pp. 1-5), original Chinese language (pp. 6-9), with claims examined (pp. 10-21), counterpart to PCT/US2006/036943, claiming priority to U.S. Appl. No. 60/719,670, pp. 1-21.
State Intellectual Property Office of China, Notification of the Second Office Action issued on Jan. 31, 2012, corresponding Patent Application No. 200680042827.2, English translation (pp. 1-5), original Chinese language (pp. 6-9), with claims examined (pp. 10-30), counterpart to PCT/US2006/036943, claiming priority to U.S. Appl. No. 60/719,670, pp. 1-30.
European Patent Office, Supplementary Partial European Search Report, issued Sep. 27, 2010, EP Application No. 06815161.2-2305, including claims, 20 pages.
Japanese Patent Office, Notice for Reasons of Refusal, mailed on Mar. 31, 2015 for corresponding Japanese Patent Application No. 039071/2013, English translation (pp. 1-4), pending claims (pp. 5-20) and original Notice in Japanese (pp. 21-23) pp. 1-23 (All references not listed below were previously submitted).
Journal of Japan Society of Pain Clinicians, 2004, vol. 11, No. 2, pp. 107-113.
The Journal of the Japanese Society for Spine Surgery and Related Research, 2001, vol. 12, No. 1, p. 1593.
Pain Clinic, 2005, vol. 26, No. 3, p. 318-325.
Canadian Intellectual Property Office, First Office Action Issued on Oct. 17, 2013 for related Canadian Patent Application No. 2,623,648 (International Patent Application No. PCT/US2006/036943) (pp. 1-5) with pending claims (pp. 6-31).
State Intellectual Property Office of the PRC, Fifth Office Action issued on Oct. 21, 2014 for related Chinese Patent Application No. 2006800428272 (International Patent Application No. PCT/US2006/036943) in English (pp. 1-8) with original Chinese OA (pp. 9-15) pp. 1-15.
Japanese Patent Office, Notice for Reasons of Refusal, mailed on Apr. 22, 2014 for corresponding Japanese Patent Application No. 039071/2013, English translation (pp. 1-4), pending claims (pp. 5-20) and original Notice in Japanese (pp. 21-24) pp. 1-24.
Barrera, P. "Scintigraphic detection of tumour necrosis factor in patients with rheumatoid arthritis," Ann Rheum Dis. Sep. 2003; 62(9), pp. 825-828.
Baraliakos, X., et al. "Magnetic Resonance Imaging Examinations of the Spine in Patients With Ankylosing Spondylitis Before and After Therapy With the Tumor Necrosis Factor alpha Receptor Fusion Protein Etanercept," Arthritis & Rheumatism, vol. 52, No. 4, Apr. 2005, pp. 1216-1223.
Marzo-Ortega, H. et al. "Efficacy of Etanercept in the Treatment of the Entheseal Pathology in Resistant Spondylarthropathy," Arthritis & Rheumatism, vol. 44, No. 9, Sep. 2001, pp. 2112-2117.
Rudwaleit, M., et al. "Prediction of a major clinical response (BASDAI 50) to tumour necrosis factor alpha blockers in ankylosing spondylitis," Ann Rheum Dis. Mar. 21, 2004, pp. 665-670.
Braun, J. et al., "Treatment of active ankylosing spondylitis with infliximab: a randomised controlled multicentre trial," The Lancet, vol. 359, Apr. 6, 2002.
Brandt, J., et al. "Six-Month Results of a Double-Blind, Placebo-Controlled Trial of Etanercept Treatment in Patients With Active Ankylosing Spondylitis," Arthritis & Rheumatism, vol. 48, No. 6, Jun. 2003, pp. 1667-1675.
Ryan, P.J., "Spinal Bone SPECT in Chronic Symptomatic Ankylosing Sponditis," Clinical Nuclear Medicine, Dec. 1997, vol. 22, No. 12, pp. 821-824.
Jacobsson, H., et al., "The application of single photon emission computed tomography to the diagnosis of ankylosing spondylitis of the spine," The British Journal of Radiology, Feb. 1984, vol. 57, pp. 133-140.
Ryan, P., "Single Photon Emission Computed Tomography and the Source of Lumbar Pain in Advanced Ankylosing Sponditis," Journal of Clinical Rheumatology, vol. 1, No. 6, Dec. 1995, pp. 323-327.
Sommer, C., "Etanercept reduces hyperalgesia in experimental painful neuropathy," Journal of the Peripheral Nervous System, vol. 6, (2001) pp. 67-72.

* cited by examiner

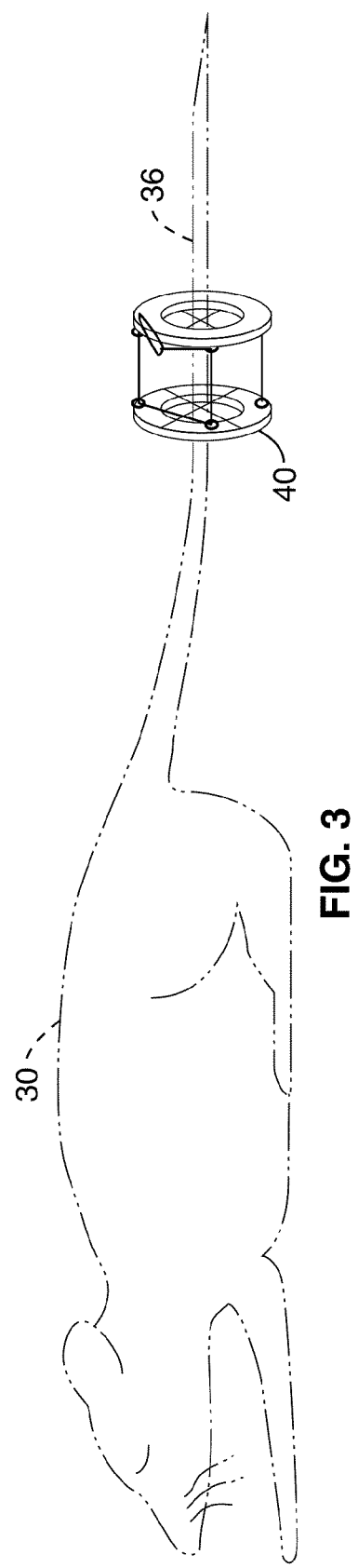

SYSTEMS, COMPOSITIONS, AND METHODS FOR LOCAL IMAGING AND TREATMENT OF PAIN

CROSS-REFERENCE TO RELATED APPLICATIONS

This patent application claims priority from, and is a 35 U.S.C. §111(a) continuation of, co-pending PCT international application serial number PCT/US2006/036943, filed on Sep. 21, 2006, incorporated herein by reference in its entirety, which claims priority from U.S. Provisional Patent Application Ser. No. 60/719,670 filed on Sep. 21, 2005, incorporated herein by reference in its entirety, and from U.S. Provisional Patent Application Ser. No. 60/750,990 filed on Dec. 15, 2005, incorporated herein by reference in its entirety.

This application is also related to PCT Publication number WO 2007/035906, published Mar. 29, 2007, incorporated herein by reference in its entirety.

STATEMENT REGARDING FEDERALLY SPONSORED RESEARCH OR DEVELOPMENT

This invention was made with Government support under Grant No. AG017762, awarded by the National Institutes of Health (NIH). The Government has certain rights in this invention.

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to imaging of tissues associated with skeletal joints. More particularly, it relates to identification and/or characterization of localized factors associated with musculoskeletal pain using labeled markers and related imaging tools.

2. Description of Related Art

Chronic back pain (i.e. generally persisting longer than 12 weeks) is among the most prevalent and expensive non-lethal conditions in the United States, and is believed to be the most common cause of disability in persons under 45 years old. The number of people suffering from chronic back pain is estimated to exceed 25% of the overall population. Every year, about 3-4% of the U.S. population is estimated to be disabled temporarily, and about 1% of the working age population is estimated to be disabled totally and permanently, due to intractable back pain. An estimated 11.7 Million patients present medically with chronic back pain. National disability expenses for this prevalent condition range from $30-$70 billion per year. Effectively treating this prevalent condition remains among the largest unmet clinical needs in medicine. Properly diagnosing and localizing the source of pain also remains a significant shortcoming on the critical path toward providing such therapy in a targeted manner with predictably successful outcomes.

Diagnosis of the location, mode, and extent of disc degeneration is often used as a precursor tool to drive therapy for treating back pain. However, such measures are often not specific enough to localize the exact site in or around a degenerating disc where pain is being experienced. Also, a direct correspondence is not always found between disc degeneration and back pain. Consequently, existing imaging modalities that identify (and even quantify) disc anatomy, such as CT or MRI, are not always helpful at localizing sources of back pain in many cases.

Accordingly, there is still a substantial need for new imaging modalities to objectively, accurately, and specifically identify and localize source(s) of pain, and in particular back pain, and still more particularly lower lumbar back pain. There is in particular such a need with respect to identifying painful discs in an improved way, and to localize within or around those discs the specific site of injury or source of pain in an improved, predictable, dependable manner.

BRIEF SUMMARY OF THE INVENTION

Accordingly, certain aspects of the present invention provide a system, composition of matter, and method that better describe, diagnose, and localize of the sources of pain in and around musculoskeletal joints, and in particular beneficial modes in and around spinal discs in relation to back pain.

Among the various modes employed according to this aspect, one particular beneficial mode involves artificially labeling substances locally in the area of back pain, such as in a particular beneficial example the spinal motion segment, that are known suspects to pain generation and transmission, such as for example disc, facet joints, and vertebral bodies.

Two particularly beneficial embodiments according to this mode, useful either alone or in combination, include: (a) labeling nerves, and in particular beneficial embodiments nociceptors, and (b) labeling chemical factors that irritate nerves, (c) labeling cells that produce chemical factors that irritate nerves; and (d) labeling blood vessels that are typically in close approximation to nerves.

In addition to the significant benefit provided by these approaches for clinical diagnosis, they are also considered highly beneficial in providing new avenues to drive choices for therapeutic approaches.

One aspect of the invention is a method for conducting a medical procedure related to a localized, active source of pain at a location within a patient. This method includes artificially labeling a pain factor at the location in a manner substantially increasing the ability to image the pain factor with an imaging tool. The labeled pain factor is then labeled in a manner sufficient to selectively differentiate a first concentration of the labeled pain factor at the location versus a second concentration of the labeled pain factor in tissue adjacent to the location.

According to one highly beneficial mode, the location is associated with a skeletal joint.

Another mode of this aspect further includes delivering a substantially targeted label into the patient that is adapted to differentially bind to and label a pain factor associated with the source of pain at the location. The pain factor at the location is artificially labeled by binding the pain factor with the targeted label.

According to one embodiment, the differential binding comprises specific binding to the pain factor.

According to another embodiment, the differential binding comprises non-specific binding to the pain factor.

According to another mode, the pain factor comprises at least one of a nerve factor, an inflammatory factor, a cellular factor, or a blood vessel factor, or a combination thereof.

In one more particular mode, the pain factor comprises a nerve factor.

According to one embodiment of this mode, the nerve factor comprises at least one substance associated with at least one of a nerve fiber or a cellular structure associated with the nerve fiber.

In another embodiment, the nerve factor comprises a substance associated with a nerve fiber. According to one particularly beneficial embodiment, the substance is in particular associated with nociceptors.

In another more particular mode, the pain factor comprises a blood vessel factor.

According to one embodiment of this mode, the blood vessel factor comprises at least one of a blood vessel or a substance or structure associated with the blood vessel.

In another embodiment of this mode, the blood vessel factor comprises a substance or structure associated with microvessels.

According to another more particular mode, the pain factor comprises a cellular factor.

According to one embodiment of this particular mode, the cellular factor is associated with a cell that produces at least one inflammatory factor.

In another embodiment, the cellular factor is associated with at least one inflammatory factor.

In another embodiment, the cellular factor is associated with cells actively producing inflammatory factors.

In another embodiment, the cellular factor is associated with an inflammatory cell of a type that is attracted to a second pain factor at the location. According to one particular variation of this embodiment, the inflammatory cell comprises a leukocyte or macrophage.

According to another more particular mode, the pain factor comprises an inflammatory factor.

According to another mode, the pain factor comprises a cytokine.

According to another mode of the present aspect, the pain factor comprises substance P or an analog or derivative or binding agent or antibody thereof.

According to another mode, the pain factor comprises CGRP or an analog or derivative or binding agent or antibody thereof.

According to another mode, the pain factor comprises receptor tyrosine kinase A (TrkA) or an analog or derivative thereof.

According to another mode, the pain factor comprises a TrkA binding agent or antibody.

According to another mode, the pain factor comprises a TrkA receptor or a binding agent or antibody thereof.

According to another mode, the pain factor comprises nerve growth factor (NGF) or an analog or derivative thereof.

According to another mode, the pain factor comprises an NGF binding agent or antibody.

According to another mode, the pain factor comprises an NGF antagonist or an analog or derivative thereof.

According to another mode, the pain factor comprises an NGF-antagonist binding agent or anti-NGF antagonist antibody.

According to another mode, the pain factor comprises a nerve binding agent or antibody or an analog or derivative thereof.

According to another mode, the pain factor comprises protein gene product 9.5 (PGP 9.5) or an analog or derivative or binding agent or antibody thereof.

According to another mode, the pain factor comprises SYN or an analog or derivative or binding agent or antibody thereof.

According to another mode, the pain factor comprises peripherin or an analog or derivative or binding agent or antibody thereof.

According to another mode, the pain factor comprises Neurofilament 200 kD (NF200) or an analog or derivative or binding agent or antibody thereof.

According to another mode, the pain factor comprises tissue necrosis factor alpha (TNF-$\alpha$) or an analog or derivative or binding agent or antibody thereof.

According to another mode, the pain factor comprises a TNF-$\alpha$ blocker or binding agent or antibody thereof.

According to another mode, the pain factor comprises macrophage migration inhibitory factor (MIF) or an analog or derivative or binding agent or antibody thereof.

According to another mode, the pain factor comprises infliximab, or an analog or derivative thereof, or a binding agent or an antibody thereof.

According to another mode, the pain factor comprises PECAM or an analog or derivative or binding agent or antibody thereof.

According to another mode, the pain factor comprises CD34 or an analog or derivative or binding agent or antibody thereof.

According to another mode, the pain factor comprises vascular cell adhesion molecule-1 (VCAM-1) or an analog or derivative or binding agent or antibody thereof.

According to another mode, the pain factor comprises an interleukin or an analog or derivative or binding agent or antibody thereof.

According to one embodiment of this mode, the interleukin comprises IL-1 or an analog or derivative or binding agent or antibody thereof.

According to another embodiment, the interleukin comprises IL-6 or an analog or derivative or binding agent or antibody thereof.

According to another embodiment, the interleukin comprises IL-8 or an analog or derivative or binding agent or antibody thereof.

According to another mode of the present aspect, the pain factor comprises prostaglandin E2 ($PGE_2$) or an analog or derivative or binding agent or antibody thereof.

According to another mode, the pain factor comprises a factor associated with pH in tissue or a binding agent or an antibody thereof.

According to one embodiment of this mode, the labeled pain factor is indicative of a relatively low pH below a predetermined threshold at the location.

According to another mode, the pain factor comprises a factor associated with pO2 in tissue or a binding agent or an antibody thereof.

In one embodiment according to this mode, the labeled pain factor is indicative of a relatively low pO2 at the location.

According to another mode, the pain factor comprises glial fibrillary acidic protein (GFAP) or an analog or derivative or binding agent or antibody thereof.

According to another mode, the pain factor comprises synuclein (SYN) or an analog or derivative or binding agent or antibody thereof.

According to another mode of the present aspect, the targeted label comprises at least one of a nerve factor, a blood vessel factor, a cellular factor, an inflammatory factor, or an antibody thereof.

According to one embodiment of this mode, the targeted label comprises a nerve factor or a binding agent or an antibody thereof.

In one variation according to this embodiment, the nerve factor comprises at least one substance associated with at least one of a nerve fiber or a cellular structure associated with the nerve fiber or an antibody thereof.

In another variation, the nerve factor comprises a substance associated with a nerve fiber or a binding agent or an antibody thereof.

In another embodiment, the targeted label comprises a blood vessel factor or a binding agent or an antibody thereof.

In one variation of this embodiment, the blood vessel factor comprises a substance associated with a structure of a blood vessel or a binding agent or an antibody thereof.

In another variation, the blood vessel factor comprises a substance associated with a structure of a microvessel or a binding agent or an antibody thereof.

According to another embodiment, the targeted label comprises a cellular factor or a binding agent or an antibody thereof.

In one variation, the cellular factor is associated with a cell that produces at least one inflammatory factor, or a binding agent or an antibody thereof.

In another variation, the cellular factor is associated with at least one inflammatory factor or a binding agent or an antibody thereof.

In another variation, the cellular factor is associated with an intervertebral disc cell that is actively producing inflammatory factors, or a binding agent or an antibody thereof.

In another variation, the cellular factor is associated with an inflammatory cell of a type that is attracted to the pain factor at the location, or a binding agent or an antibody thereof.

According to one feature of this variation, the inflammatory cell comprises a leukocyte, or a binding agent or an antibody thereof.

According to another embodiment, the targeted label comprises an inflammatory factor, or a binding agent or an antibody thereof.

In one variation of this embodiment, the inflammatory factor comprises a cytokine, or an analog or derivative thereof, or a binding agent or an antibody thereof.

According to another mode of the present aspect, the targeted label comprises a binding agent or antibody to substance P.

According to another mode, the targeted label comprises a binding agent or antibody to calcitonin gene-related peptide (CGRP).

According to another mode, the targeted label comprises a TrkA antibody or binding agent.

According to another mode, the targeted label comprises nerve growth factor (NGF), or an analog or derivative thereof.

According to another mode, the targeted label comprises a NGF binding agent or an anti-NGF antibody.

According to another mode, the targeted label comprises a NGF antagonist or a binding agent or an antibody thereof.

According to another mode, the targeted label comprises an anti-NGF antagonist antibody or binding agent.

According to another mode, the targeted label comprises a nerve antibody or binding agent.

According to another mode, the targeted label comprises PGP 9.5, or an analog or derivative thereof, or a binding agent or an antibody thereof.

According to another mode, the targeted label comprises a binding agent or antibody to peripherin.

According to another mode, the targeted label comprises Neurofilament 200 kD (NF200), or an analog or derivative thereof, or a binding agent or an antibody thereof.

According to another mode, the targeted label comprises TNF-α, or an analog or derivative thereof, or a binding agent or an antibody thereof.

According to another mode, the targeted label comprises a TNF-α blocker.

According to another mode, the targeted label comprises infliximab, or an analog or derivative thereof, or a binding agent or an antibody thereof.

According to another mode, the targeted label comprises a PECAM binding agent or antibody.

According to another mode, the targeted label comprises a binding agent or antibody to CD34.

According to another mode, the targeted label comprises an interleukin binding agent or antibody.

In one embodiment of this mode, the interleukin binding agent or antibody comprises an IL-1 binding agent or antibody.

In another embodiment of this mode, the interleukin binding agent or antibody comprises an IL-6 binding agent or antibody.

In another embodiment of this mode, the interleukin binding agent or antibody comprises an IL-8 binding agent or antibody.

According to another mode of the present aspect, the targeted label comprises a binding agent or antibody to $PGE_2$.

According to another mode, the targeted label comprises a binding agent or antibody to MIF.

According to another mode, the targeted label comprises an antibody or binding agent to a factor associated with pH in tissue.

According to one embodiment of this mode, the labeled pain factor is indicative of a relatively low pH below a predetermined threshold at the location.

According to another mode, the targeted label comprises an antibody or binding agent to a factor associated with pO2 in tissue.

According to one embodiment of this mode, the labeled pain factor is indicative of a relatively low pO2 at the location.

According to another mode, the targeted label comprises a radioactive material.

According to one embodiment of this mode, the targeted label comprises a radio-labeled TNF-α antibody, or an analog or derivative thereof.

According to another embodiment, the targeted label comprises radiolabeled iodine. In one variation of this embodiment, the radiolabeled iodine comprises I-125.

According to another mode, the targeted label comprises a nanoparticle.

According to another mode, the targeted label comprises gold.

According to another mode, the targeted label comprises iron oxide.

According to another mode, the targeted label comprises gadolinium.

According to another mode of the present aspect, the method further includes imaging the labeled pain factor using an imaging tool that comprises a phosphor imaging plate.

According to another mode, the method includes imaging the labeled pain factor using MRI.

According to another mode, a first binding agent is delivered into the body that is adapted to bind to a first pain factor. The targeted label is delivered into the patient's body after the first binding agent is bound to the first pain factor. The targeted label is adapted to bind to a site located on the bound combination of the first binding agent and the first pain factor.

According to one embodiment, the first binding agent comprises a bi-specific antibody with a first binding site adapted to bind to the first pain factor and a second binding site adapted to bind to the targeted label.

According to another mode, the targeted label comprises a cell bound to an antibody having an exposed binding site that is adapted to bind to the pain factor.

According to another mode, the method further includes conducting a therapeutic procedure in a substantially localized manner to the location where the targeted labeled pain factor is locally imaged.

In one embodiment of this mode, the therapeutic procedure is adapted to substantially alleviate generation or transmission of pain at the location.

According to another embodiment, the therapeutic procedure is adapted to substantially ablate at least one nerve at the location.

In another embodiment, the therapeutic procedure comprises delivering at least one therapeutic chemical in a substantially localized manner to the location.

In another embodiment, the therapeutic procedure comprises delivering a therapeutic dose of energy in a substantially localized manner to the location.

In one variation of this embodiment, the therapeutic procedure further comprises ablating at least one nerve at the location with the therapeutic dose of energy.

In another variation, the therapeutic procedure further comprises delivering ultrasound energy to the location. In a further variation, the method further includes delivering the ultrasound energy in a directed manner locally into the location from a second location. In still a further variation, the second location is outside of the patient, and the ultrasound energy is delivered via high intensity focused ultrasound (HIFU) that is adapted to focus the ultrasound energy to the location. In yet another variation, the second location is adjacent to the location within the patient, and the ultrasound energy is delivered via a directional ultrasound probe. In still a further feature of this variation, the second location is adjacent to an intervertebral disc and the location receiving the directional ultrasound therapy is within the intervertebral disc.

According to another variation of the present embodiment, the therapeutic dose of energy comprises thermal energy.

According to another variation, the therapeutic dose of energy comprises electrical energy. In one further variation, the method involves delivering the electrical energy via a radiofrequency (RF) probe.

According to another variation, the therapeutic dose of energy comprises microwave energy.

According to another variation, the therapeutic dose of energy comprises light energy.

According to another mode of the present aspect, the location comprises at least a portion of an intervertebral disc.

According to another mode, the location comprises a region of tissue located within only a portion that is equal to less than an entire circumference of an intervertebral disc.

In one embodiment of this mode, the portion comprises a region of tissue located within less than or equal to one-half of the circumference of the intervertebral disc.

In one variation of this embodiment, the portion comprises a region of tissue located within less than or equal to one-quarter of a circumference of the intervertebral disc.

According to another mode of the present aspect of the invention, the location comprises an end-plate associated with a vertebral body.

According to another mode, the location comprises a facet joint.

The method of the present aspect according to another mode includes delivering the targeted label in a localized manner to the location.

One embodiment of this mode further includes injecting the targeted label into a region of tissue associated with the location using a local injection assembly.

Another embodiment includes delivering the targeted label systemically to the patient.

One further embodiment includes injecting the targeted label into the patient's systemic blood circulation.

Another further embodiment includes delivering the targeted label into the patient's gastrointestinal system.

Another mode includes artificially labeling the pain factor at multiple said locations by binding the pain factor with the targeted label delivered into the patient. The labeled pain factor is then imaged with an imaging tool adapted to image at least one of the targeted label or the labeled pain factor and in a manner sufficient to differentiate a first concentration of the labeled pain factor at the multiple said locations versus a second concentration of the labeled pain factor in tissue adjacent to the multiple said locations.

According to one embodiment of this mode, the method further includes conducting at least one therapeutic procedure in a substantially localized manner to each of the locations where the targeted labeled pain factor is locally and selectively imaged.

According to another mode of this present aspect, the pain factor comprises MIF or a binding agent or antibody thereof.

According to another mode of this aspect, the targeted agent comprises an MIF binding agent or antibody.

According to another mode of the present aspect, the targeted agent comprises a nanoparticle.

According to another mode of the present aspect, the targeted agent comprises at least one of gold or iron oxide.

According to another mode of the present aspect, the targeted agent comprises an MRI contrast agent.

According to one embodiment of the preceding mode, the MRI contrast agent comprises gadolinium.

According to another embodiment of the present mode, the method further comprises MRI imaging an area of increased concentration of the MRI contrast agent bound to the pain factor.

According to another mode of the present aspect, the targeted agent comprises an ultrasound contrast agent.

According to one embodiment of this mode, the method further comprises ultrasonically imaging an area of increased concentration of the ultrasound contrast agent bound to the pain factor.

According to another mode of the present aspect, the targeted agent comprises a radiographic contrast agent.

According to one embodiment of this mode, the method further comprises imaging an area of increased concentration of the radiographic contrast agent bound to the pain factor using X-ray.

According to another mode of the present aspect, the method further comprises imaging a location of the targeted agent bound to the pain factor in a manner allowing for enhanced localized therapy to the location.

According to another mode of the present aspect, the method further comprises delivering the targeted agent into the patient via the patient's respiratory system.

Another aspect of the invention involves a system for treating pain at a location within a body of a patient. This aspect includes a targeted agent that comprises a targeted label that is adapted to bind to and label a pain factor associated with a source of pain at the location. Also included is a delivery assembly that is adapted to deliver the targeted label into the patient. An imaging system also included in the system is adapted to image at least one of the targeted label or the labeled pain factor and in a manner sufficient to selectively differentiate a first concentration of the labeled pain factor at the location versus a second concentration of the labeled pain factor in tissue adjacent to the location. A therapeutic device assembly is also included, and is adapted to provide therapy in a substantially localized manner that is substantially isolated to the location.

According to one mode of this aspect, the targeted label is adapted to bind and label a pain factor associated musculoskeletal joint pain, and the location is associated with at least one musculoskeletal joint.

According to one embodiment, the therapeutic device assembly comprises an energy delivery assembly that is adapted to deliver a therapeutic dose of energy in a substantially localized manner that is substantially isolated to the location associated with the musculoskeletal joint.

According to one further embodiment, the energy delivery assembly is adapted to be delivered into the patient to a position at or adjacent to the location.

According to another further embodiment, an introducer is provided in the system and is adapted to deliver the energy delivery assembly to the location.

In one variation of this embodiment, the introducer comprises a needle assembly. This may provide the additional feature in that the needle assembly is adapted to be advanced through bone and to deliver the therapeutic device assembly to a position within the bone. According to another further feature, the therapeutic device assembly may be adapted to ablate an intraosseous nerve within the bone and that is associated with pain related to the labeled pain factor visualized at the location. In another further beneficial feature, the needle assembly is adapted to be advanced through bone of a vertebral body and to deliver the therapeutic device assembly to a position within the vertebral body associated with a basivertebral nerve, and the therapeutic device assembly is adapted to ablate the basivertebral nerve from the position.

According to another mode of the present aspect, the therapeutic device assembly comprises a radiofrequency (RF) current ablation assembly.

In one embodiment, the RF current ablation assembly comprises a first electrode and a second electrode adapted to be positioned at first and second positions adapted to straddle at least a portion of the basivertebral nerve. The RF current ablation assembly is adapted to deliver the RF current between the first and second electrodes sufficient to ablate nerve tissue between the first and second positions.

According to one variation of this embodiment, the RF current ablation assembly comprises a delivery probe with an elongated body that carries the first and second electrodes in a bipolar lead assembly arrangement.

According to another mode of the present embodiment, the targeted label is adapted to bind and label a pain factor comprising at least one of a nerve factor, a blood vessel factor, a cellular factor, an inflammatory factor, or an antibody thereof.

It is to be appreciated that further more detailed particularly beneficial modes provided hereunder are contemplated with respect to the present aspect described. In particular, further modes of the present aspect include the various beneficial examples for pain factors and targeted labels described for use under the method aspect of the invention described above.

According to one further mode of the present aspect, the targeted label is adapted to selectively bind and label a pain factor that comprises at least one of Substance P, CGRP, trkA, NGF, an NGF antagonist, PGP 9.5, SYN, peripherin, Neurofilament 200 kD (NF200), PECAM, CD34, GFAP, an interleukin, a leukocyte, a cytokine, TNF-α, MIF, an analog or derivative thereof, or a binding agent or antibody thereof.

According to another mode of the present aspect, the targeted label comprises a binding agent or antibody of at least one of Substance P, CGRP, trka, NGF, an NGF antagonist, PGP 9.5, SYN, peripherin, Neurofilament 200 kD (NF200), PECAM, CD34, GFAP for endothelial cells, an interleukin, a leukocyte, a cytokine, TNF-α, or MIF, or comprises NGF, NF200, PGP 9.5, or an analog or derivative thereof.

According to another mode of the present aspect, the targeted label is adapted to bind and label TNF-α or a binding agent or an antibody thereof.

According to another mode of the present aspect, the targeted label comprises a labeled TNF-α antibody or binding agent.

According to another mode of the present aspect, the targeted label comprises infliximab, or an analog or derivative thereof, or a binding agent or antibody thereof.

According to another mode of the present aspect, the targeted label comprises a radioactive material. According to one embodiment of this mode, the targeted label comprises a radio-labeled TNF-α antibody, or an analog or derivative thereof. According to another embodiment of this mode, the targeted label comprises radiolabeled iodine. According to one variation of this embodiment, the radiolabeled iodine comprises I-125.

According to another mode, the system further includes an imaging tool that is adapted to image the labeled pain factor in a manner sufficient to differentiate a first concentration at the location associated with pain versus a second concentration at a second location adjacent to the location and associated with less pain than at the location.

According to another mode of the present aspect, the pain factor comprises MIF or a binding agent or antibody thereof. According to another mode, the targeted agent comprises an MIF binding agent or antibody. According to still another mode, the targeted agent comprises a nanoparticle. According to yet still another mode, the targeted agent comprises at least one of gold or iron oxide.

According to another mode of the present aspect, the targeted agent comprises an MRI contrast agent. According to one embodiment of this mode, the MRI contrast agent comprises gadolinium. According to another embodiment, the system further comprises an MRI system configured for MRI imaging an area of increased concentration of the MRI contrast agent bound to the pain factor.

According to another mode of the present aspect, the targeted agent comprises an ultrasound contrast agent. According to one embodiment of this mode, the system further comprises an ultrasound imaging system configured for ultrasonically imaging an area of increased concentration of the ultrasound contrast agent bound to the pain factor.

According to still another mode of the present aspect, the targeted agent comprises a radiographic contrast agent. In one embodiment of this mode, the system further comprises an X-ray imaging system configured for X-ray imaging an area of increased concentration of the radiographic contrast agent bound to the pain factor.

Another aspect of the invention is a method for imaging and identifying a localized, active source of pain at a location associated with a region of tissue in a patient, such as in particular beneficial further modes a skeletal joint in a patient, and in still further beneficial more detailed modes spinal joints in a patient. This method includes delivering a substantially targeted label into the patient that is adapted to differentially bind to and label a pain factor. A pain factor that is resident at the location is artificially labeled by binding the pain factor with the targeted label delivered into the patient. The labeled pain factor is imaged with an imaging tool adapted to image at least one of the label or the labeled pain factor and in a manner sufficient to differentiate a first concentration of the labeled pain factor at the location versus a second concentration of the labeled pain factor in tissue adjacent to the location.

According to various modes of this aspect, the pain factor may be related to at least one of a nerve fiber, a substance associated with a nerve fiber, a blood vessel, a substance associated with a blood vessel, a cell actively producing at least one inflammatory factor, a cell attracted to inflammation or other pain factors, or a chemo-inflammatory factor, or a combination thereof.

Another aspect of the invention is a system for identifying or characterizing a property of tissue associated with a skeletal joint. Such aspect may further include any one or more of the various aspects, modes, embodiments, variations, or features herein shown or described, or combinations thereof.

According to one mode of this aspect, the system is adapted to provide information indicative of a degree of a property of at least a portion of an intervertebral disc.

Another aspect is a system for identifying or characterizing a property of tissue associated with a skeletal joint in a patient. This includes labeling at least one of: pain factors, nerve factors, blood vessel factors, cellular factors, or inflammation factors. Or, the system may include a combination of one or more of the foregoing.

According to one mode of this aspect, the information is related to a degree of a property of at least a portion of an intervertebral disc.

Another aspect of the invention is a system for characterizing at least a portion of an intervertebral disc with respect to a degree of a property of that disc, such as in particular related to pain or degeneration. This system includes a labeled marker delivery system and a labeled marker imaging system. The labeled marker imaging system provides information that is useful to indicate at least in part the degree of the property.

According to one further embodiment of the foregoing aspects and modes, the respective system is adapted to produce the information based on either or both of an annular portion or a nucleus portion of the intervertebral disc.

According to another embodiment, the system is adapted to display a geographical representation related to the spatial concentration of the labeled factor, and a portion of the geographical representation provides the information.

According to another embodiment, the information is adapted to distinguish a degree of degradation of the disc. According to one highly beneficial further embodiment, the information is adapted to distinguish as to the degree of degradation by reference to a Thompson scale.

According to another embodiment, the property comprises at least one of pain, or at least one factor that correlates with pain.

According to another embodiment, the information is related to ratios of concentration of one or more pain factors.

According to another embodiment, the information is related to presence of secondary or other indirect materials that generally, though indirectly, correlate well with presence of other more direct pain factors.

According to another embodiment, the information relates to at least one chemical constituent of an intervertebral disc.

According to another embodiment, the property comprises at least one of a degree of dehydration of the disc, a degree of breakdown of a proteoglycan matrix of the disc, and a degree in a breakdown of a collagen matrix.

According to another embodiment, the system further includes a radiolabel imaging system that is adapted to produce the information.

Another aspect of the invention is a method for identifying or characterizing a property of tissue associated with a skeletal joint. One or more of the foregoing method aspects, modes, embodiments, variations, or features herein described, or combinations thereof, may be employed to advance this method.

One further mode of this aspect further includes providing information indicative of a degree of a property of at least a portion of an intervertebral disc.

Another aspect is a method for identifying or characterizing a property of tissue associated with a skeletal joint in a patient, and includes at least one of the following steps: labeling a pain factor in the tissue; imaging the labeled pain factor in the tissue; comparing different imaged regions having different concentrations of the labeled pain factor; identifying a location of increased presence of pain factors based upon the comparison; and treating the location with local treatment modality based upon the identification. Or a combination of one or more of the foregoing may be used.

One mode of this aspect includes determining a degree of a property of at least a portion of an intervertebral disc based upon the information.

Another aspect of the invention is a method for characterizing at least a portion of an intervertebral disc with respect to a degree of a property thereof, and includes capturing a signal related to the portion using a signal imaging system. The signal imaging system provides information that indicates at least in part the degree of the property.

According to one embodiment of the various method aspects and modes just described, the information produced is based on either or both of an annular portion or a nucleus portion of the intervertebral disc.

In another embodiment, a curve is displayed that is related to the presence of the labeled pain factor, and wherein a portion of the curve provides the information.

Another embodiment includes distinguishing a degree of degradation of the disc based upon the information. A still further embodiment includes distinguishing the degree of degradation of the disc in relation to a Thompson grade based upon the information.

Another embodiment includes correlating the disc with degree of pain, or at least one factor that correlates with pain, based upon the information.

According to another embodiment, the information is related to a ratio of magnitude of a signal imaged that corresponds with the amount of labeled pain factor in a given area or volume of tissue.

According to another embodiment, the information is related to a cytokine, a precursor material thereof, an analog or derivative thereof, or a metabolite or degradation product thereof.

According to another embodiment, the information relates to at least one chemical constituent of an intervertebral disc.

According to another embodiment, the property relates to at least one of a degree of dehydration of the disc, a degree of breakdown of a proteoglycan matrix of the disc, and a degree in a breakdown of a collagen matrix.

Another embodiment includes producing the information at least in part using a radiation imaging system.

Another aspect is a method for preparing a system for performing a medical procedure on a patient, comprising: diagnosing the patient with pain; and based upon the diagnosis, preparing a volume of a targeted agent for delivery into the patient. The prepared volume of targeted agent is configured to differentially bind to a pain factor associated with the pain in a manner adapted to enhance at least one of (i) diagnostic localization of the pain and (ii) selective tissue therapy in an area associated with the bound pain factor in response to a delivered energy to the area.

According to one mode of this aspect, the pain factor comprises MIF or a binding agent or antibody thereof.

According to another mode of this aspect, the targeted agent comprises an MIF binding agent or antibody.

According to another mode of the present aspect, the targeted agent comprises a nanoparticle.

According to another mode of the present aspect, the targeted agent comprises at least one of gold or iron oxide.

According to another mode of the present aspect, the targeted agent comprises an MRI contrast agent.

According to one embodiment of the preceding mode, the MRI contrast agent comprises gadolinium.

According to another embodiment of the present mode, the method further comprises MRI imaging an area of increased concentration of the MRI contrast agent bound to the pain factor.

According to another mode of the present aspect, the targeted agent comprises an ultrasound contrast agent.

According to one embodiment of this mode, the method further comprises ultrasonically imaging an area of increased concentration of the ultrasound contrast agent bound to the pain factor.

According to another mode of the present aspect, the targeted agent comprises a radiographic contrast agent.

According to one embodiment of this mode, the method further comprises imaging an area of increased concentration of the radiographic contrast agent bound to the pain factor using X-ray.

According to another mode of the present aspect, the method further comprises imaging a location of the targeted agent bound to the pain factor in a manner allowing for enhanced localized therapy to the location.

According to another mode of the present aspect, the method further comprises delivering the targeted agent into the patient via the patient's respiratory system.

Another aspect is a system for performing a medical procedure on a patient, comprising: a therapeutic volume of a targeted agent prepared for delivery into a patient diagnosed with pain and that is configured to differentially bind to a pain factor associated with the pain in a manner adapted to enhance at least one of (i) diagnostic localization of the pain and (ii) selective tissue therapy to a location containing the bound pain factor in response to a delivered energy to an area containing the location.

According to one mode of the present aspect, the pain factor comprises MIF or a binding agent or antibody thereof. According to another mode, the targeted agent comprises an MIF binding agent or antibody. According to still another mode, the targeted agent comprises a nanoparticle. According to yet still another mode, the targeted agent comprises at least one of gold or iron oxide.

According to another mode of the present aspect, the targeted agent comprises an MRI contrast agent. According to one embodiment of this mode, the MRI contrast agent comprises gadolinium. According to another embodiment, the system further comprises an MRI system configured for MRI imaging an area of increased concentration of the MRI contrast agent bound to the pain factor.

According to another mode of the present aspect, the targeted agent comprises an ultrasound contrast agent. According to one embodiment of this mode, the system further comprises an ultrasound imaging system configured for ultrasonically imaging an area of increased concentration of the ultrasound contrast agent bound to the pain factor.

According to still another mode of the present aspect, the targeted agent comprises a radiographic contrast agent. In one embodiment of this mode, the system further comprises an X-ray imaging system configured for X-ray imaging an area of increased concentration of the radiographic contrast agent bound to the pain factor.

Another aspect is a method for selectively treating one or more tissue regions associated with pain in a patient, comprising delivering a targeted agent into the patient configured to differentially bind to a pain factor associated with the pain; and allowing the delivered targeted agent to differentially bind to the pain factor so as to form a differentially bound pain factor; and delivering energy into the patient in a manner that differentially treats the one or more regions associated with the differentially bound pain factor.

According to one mode of this aspect, the pain factor comprises MIF or a binding agent or antibody thereof.

According to another mode of this aspect, the targeted agent comprises an MIF binding agent or antibody.

According to another mode of the present aspect, the targeted agent comprises a nanoparticles.

According to another mode of the present aspect, the targeted agent comprises at least one of gold or iron oxide.

According to another mode of the present aspect, the targeted agent comprises an MRI contrast agent.

According to one embodiment of the preceding mode, the MRI contrast agent comprises gadolinium.

According to another embodiment of the present mode, the method further comprises MRI imaging an area of increased concentration of the MRI contrast agent bound to the pain factor.

According to another mode of the present aspect, the targeted agent comprises an ultrasound contrast agent.

According to one embodiment of this mode, the method further comprises ultrasonically imaging an area of increased concentration of the ultrasound contrast agent bound to the pain factor.

According to another mode of the present aspect, the targeted agent comprises a radiographic contrast agent.

According to one embodiment of this mode, the method further comprises imaging an area of increased concentration of the radiographic contrast agent bound to the pain factor using X-ray.

According to another mode of the present aspect, the method further comprises imaging a location of the targeted agent bound to the pain factor in a manner allowing for enhanced localized therapy to the location.

According to another mode of the present aspect, the method further comprises delivering the targeted agent into the patient via the patient's respiratory system.

Another aspect is a system for selectively treating one or more tissue regions associated with pain in a patient, comprising: a volume of targeted agent; and an energy delivery system that is configured to deliver energy into the patient. The volume of targeted agent is configured for delivery into a patient and to differentially bind to a pain factor associated with the pain in a manner such that tissue regions containing a first concentration of the differentially bound pain factor exhibit a differential and selective therapeutic response to the delivered energy versus other regions with lower concentrations of the differentially bound pain factor.

According to one mode of the present aspect described immediately above, the pain factor comprises MIF or a binding agent or antibody thereof. According to another mode, the targeted agent comprises an MIF binding agent or antibody. According to still another mode, the targeted agent comprises a nanoparticle. According to yet still another mode, the targeted agent comprises at least one of gold or iron oxide.

According to another mode of the present aspect, the targeted agent comprises an MRI contrast agent. According to one embodiment of this mode, the MRI contrast agent comprises gadolinium. According to another embodiment, the system further comprises an MRI system configured for MRI imaging an area of increased concentration of the MRI contrast agent bound to the pain factor.

According to another mode of the present aspect, the targeted agent comprises an ultrasound contrast agent. According to one embodiment of this mode, the system further comprises an ultrasound imaging system configured for ultrasonically imaging an area of increased concentration of the ultrasound contrast agent bound to the pain factor.

According to still another mode of the present aspect, the targeted agent comprises a radiographic contrast agent. In one embodiment of this mode, the system further comprises an X-ray imaging system configured for X-ray imaging an area of increased concentration of the radiographic contrast agent bound to the pain factor.

Another aspect of the invention is a method of performing a medical procedure on a patient, comprising: delivering a material to a region within a body of a patient; wherein the material has a preferential binding affinity to a pain factor located within the region sufficient to preferentially bind to the pain factor versus other structures within the region, and such that the material accumulates at a higher concentration within a first portion of the region having a higher amount of the pain factor than other portions within the region; and after delivering the material to the region, delivering energy to the region in a manner that selectively treats the first portion versus the other portions and such that pain is reduced in the region.

According to one mode of the method just described, the material comprises a metal. In one embodiment of this mode, the material comprises gold. In another embodiment of this mode, the material comprises a nanoparticle. In still another embodiment, the material comprises a gold nanoparticle.

According to another mode of the present method aspect, the material comprises an antibody.

In another mode of this aspect, the material comprises an antibody and a metal associated with the antibody. According to one embodiment of this mode, the material comprises an antibody and a metal nanoparticle associated with the antibody. In a further variation of this embodiment, the material comprises an antibody and a gold nanoparticle associated with the antibody.

According to another mode of the present method aspect, the region comprises a skeletal joint.

According to still another mode of the present method aspect, the region comprises at least a portion of a spine. In one embodiment of this mode, the first portion comprises at least one spinal joint level along the spine, and the other portions comprise at least one other spinal joint level along the spine. In another embodiment of this mode, the first portion comprises a single spinal joint. In still another embodiment of this mode, the region comprises at least an area of a spinal joint. In one variation of this embodiment, the first portion comprises at least part of an intervertebral disc. In another variation, the first portion comprises at least part of a vertebral body. In still another variation, the first portion comprises at least part of a vertebral body endplate. In yet another further variation, the first portion comprises a facet joint. In another variation, the first portion comprises a transverse process.

According to another mode of the present method aspect, the pain factor comprises at least one of: a nerve factor, a blood vessel factor, a microvessel factor, a cellular factor, an inflammatory factor, a cell that produces at least one inflammatory factor, a cellular factor associated with an intervertebral disc cell that is actively producing inflammatory factors, a cellular factor associated with an inflammatory cell of a type that is attracted to a second pain factor at the location, a leukocyte, a cytokine, substance P, CGRP, trkA, nerve growth factor (NGF), an NGF receptor, an NGF antagonist, PGP 9.5, SYN, peripherin, Neurofilament 200 kD (NF200), TNF-$\alpha$, a TNF-$\alpha$ blocker, a TNF-$\alpha$ receptor, infliximab, PECAM, CD34, GFAP, interleukin, IL-1, IL-6, IL-8, PGE-2, a factor associated with pH in tissue, a factor associated with pO2 in tissue, a binding agent or antibody thereof, a receptor thereof, an analog thereof, and a derivative thereof.

According to still another mode of the present method aspect, the method further comprises imaging the region in a manner that sufficiently differentiates spatial relationships between different concentrations of the material so as to substantially identify the location of the first portion relative to the other portions within the region.

According to one embodiment of this mode, the method further comprises delivering the energy principally to the first portion in a substantially localized manner sufficient to differentially treat the first portion with the energy versus the other portions.

According to another mode of the present method aspect, the method further comprises diagnosing the patient in a manner that identifies the region as a painful region of the patient's body.

According to yet another mode of the present method aspect, the portion is not diagnosed to include cancer cells prior to conducting the medical procedure.

According to another mode of this present aspect, the pain factor comprises MIF or a binding agent or antibody thereof.

According to another mode of this aspect, the targeted agent comprises an MIF binding agent or antibody.

According to another mode of the present aspect, the targeted agent comprises a nanoparticles.

According to another mode of the present aspect, the targeted agent comprises at least one of gold or iron oxide.

According to another mode of the present aspect, the targeted agent comprises an MRI contrast agent.

According to one embodiment of the preceding mode, the MRI contrast agent comprises gadolinium.

According to another embodiment of the present mode, the method further comprises MRI imaging an area of increased concentration of the MRI contrast agent bound to the pain factor.

According to another mode of the present aspect, the targeted agent comprises an ultrasound contrast agent.

According to one embodiment of this mode, the method further comprises ultrasonically imaging an area of increased concentration of the ultrasound contrast agent bound to the pain factor.

According to another mode of the present aspect, the targeted agent comprises a radiographic contrast agent.

According to one embodiment of this mode, the method further comprises imaging an area of increased concentration of the radiographic contrast agent bound to the pain factor using X-ray.

According to another mode of the present aspect, the method further comprises imaging a location of the targeted agent bound to the pain factor in a manner allowing for enhanced localized therapy to the location.

According to another mode of the present aspect, the method further comprises delivering the targeted agent into the patient via the patient's respiratory system.

Another aspect of the present invention is a system for treating a patient, comprising: a volume of material that comprises a metal; wherein the material exhibits a binding affinity to a pain factor such that when the material is delivered to a region within a body of a patient that includes the pain factor the material differentially binds to the pain factor with more affinity than to other structures within the region, and such that the material accumulates at a higher concentration within a first portion of the region having a higher amount of the pain factor than other portions within the region; and an energy source that is adapted to deliver energy to the region in a manner that substantially locally treats the first portion versus the other portions.

According to one mode of this present aspect just described immediately above, the metal comprises gold.

According to another mode of this present aspect, the metal comprises a metal nanoparticle.

According to another mode of this present aspect, the metal comprises a gold nanoparticle.

According to another mode of this present aspect, the system further comprises an imaging system that is adapted to image the material in a manner that is adapted to sufficiently differentiate spatial relationships between different concentrations of the material so as to identify the location of the first portion relative to the other portions within the region.

According to still another mode of this present aspect, the material is adapted to preferentially bind to a pain factor that further comprises: a nerve factor, a blood vessel factor, a microvessel factor, a cellular factor, an inflammatory factor, a cell that produces at least one inflammatory factor, a cellular factor associated with an intervertebral disc cell that is actively producing inflammatory factors, a cellular factor associated with an inflammatory cell of a type that is attracted to a second pain factor at the location, a leukocyte, a cytokine, substance P, CGRP, trkA, nerve growth factor (NGF), an NGF receptor, an NGF antagonist, PGP 9.5, SYN, peripherin, Neurofilament 200 kD (NF200), TNF-α, a TNF-α blocker, a TNF-α receptor, infliximab, PECAM, CD34, GFAP for endothelial cells, interleukin, IL-1, IL-6, IL-8, PGE-2, a factor associated with pH in tissue, a factor associated with pO2 in tissue, a binding agent or an antibody thereof, a receptor thereof, an analog thereof, and a derivative thereof.

According to still another mode of this present aspect, the material comprises an antibody of at least one of the pain factors provided in the immediately preceding mode.

According to another mode of the present aspect, the pain factor comprises MIF or a binding agent or antibody thereof. According to another mode, the targeted agent comprises an MIF binding agent or antibody. According to still another mode, the targeted agent comprises a nanoparticle. According to yet still another mode, the targeted agent comprises at least one of gold or iron oxide.

According to another mode of the present aspect, the targeted agent comprises an MRI contrast agent. According to one embodiment of this mode, the MRI contrast agent comprises gadolinium. According to another embodiment, the system further comprises an MRI system configured for MRI imaging an area of increased concentration of the MRI contrast agent bound to the pain factor.

According to another mode of the present aspect, the targeted agent comprises an ultrasound contrast agent. According to one embodiment of this mode, the system further comprises an ultrasound imaging system configured for ultrasonically imaging an area of increased concentration of the ultrasound contrast agent bound to the pain factor.

According to still another mode of the present aspect, the targeted agent comprises a radiographic contrast agent. In one embodiment of this mode, the system further comprises an X-ray imaging system configured for X-ray imaging an area of increased concentration of the radiographic contrast agent bound to the pain factor.

Each aspect, mode, embodiment, variation, or feature herein described is considered independently beneficial without requiring combination with the others. However, such further combinations and sub-combinations thereof are also considered yet further beneficial independent aspects invention. For example, where particular modes, embodiments, variations, or features are herein described with respect to one aspect hereunder, it is to be appreciated by one of ordinary skill that such description is further applicable to other aspects also described though such particular combination may not be specifically mentioned. In further example, a more detailed description provided with respect to a method aspect may provide information that is to be clearly combined as further development of a similar system-related aspect or description, or visa versa.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 1 shows a schematic of certain cascades associated with inflammation and pain.

FIGS. 2A-D shows stained cross-sectioned histology slides indicating presence of certain factors associated with pain as follows, wherein "N" is nucleus pulposus, "A" is annulus fibrosus, and "G" designates growth plate.

FIG. 3 shows a schematic view of a mouse 30 according to an experimental model wherein the mouse tail 36 is injured by a fixture 40 for evaluating pain factors.

Figure 4:
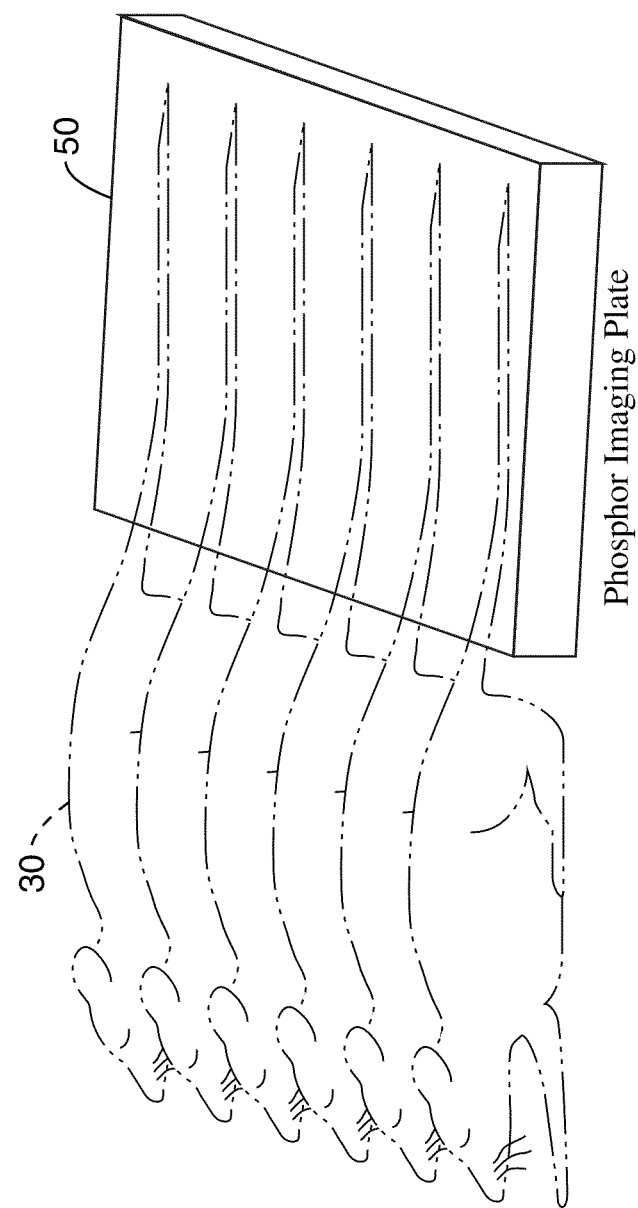

FIG. 4 shows an experimental set-up related to the mouse injury model illustrated in FIG. 3, wherein a series of mice 30 are positioned for viewing their respective tails via a phosphor imaging plate 50.

Figure 5:
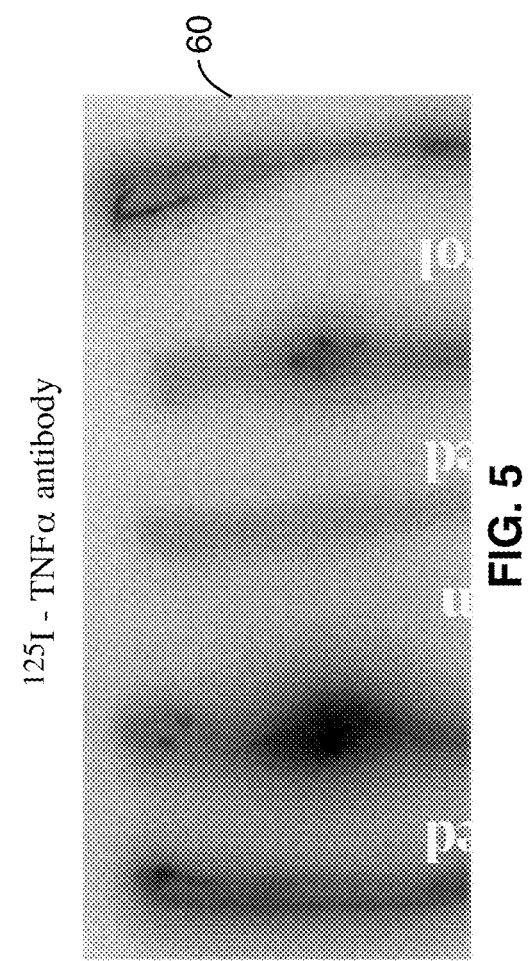

FIG. 5 shows an image 60 taken from a phosphor imaging plate according to the set-up shown in FIG. 4 for four treatment mice and one control mouse tail (located centrally in the figure).

Figure 6:
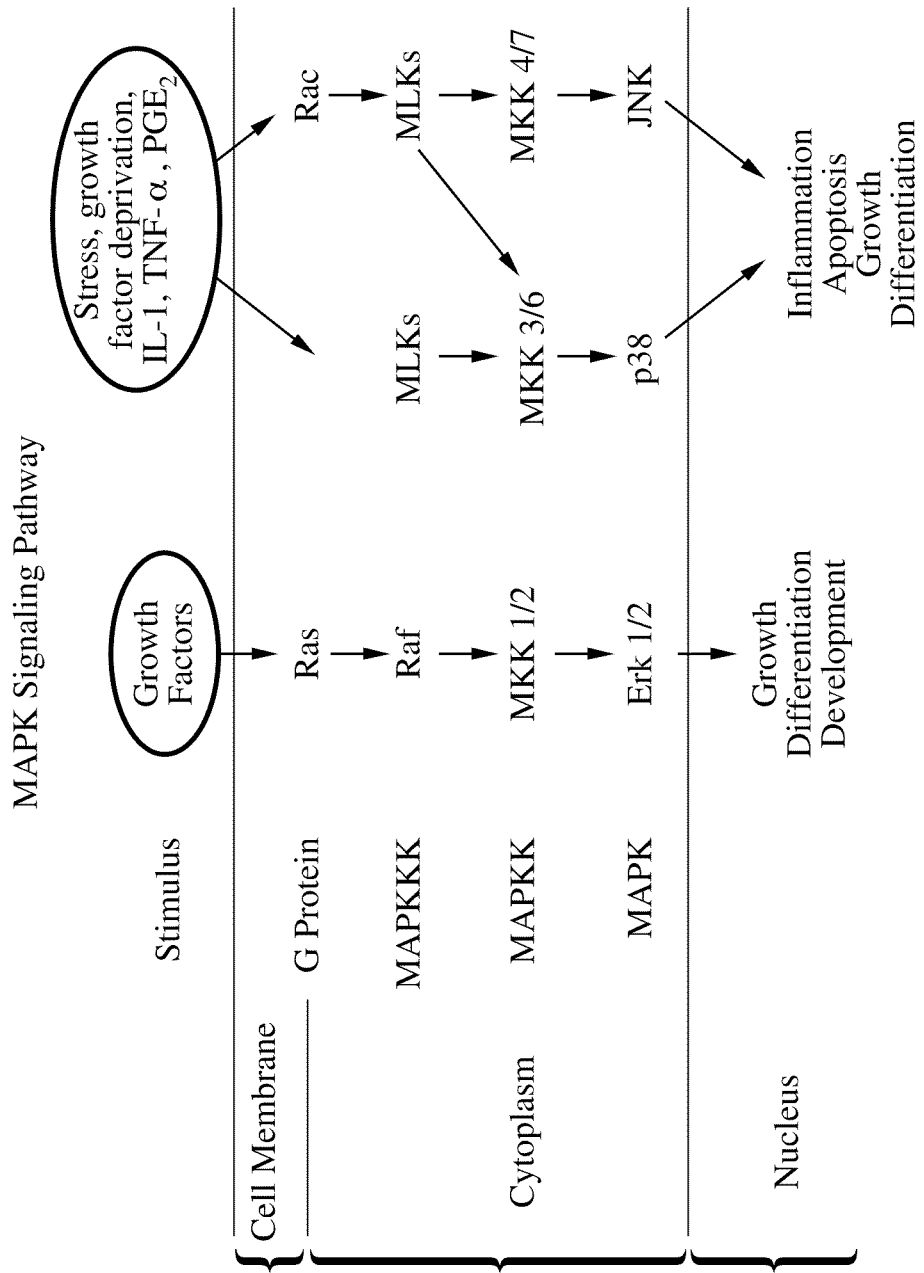

FIG. 6 shows a schematic view of MAPK signaling pathways associated with certain pain factors.

Figure 7:
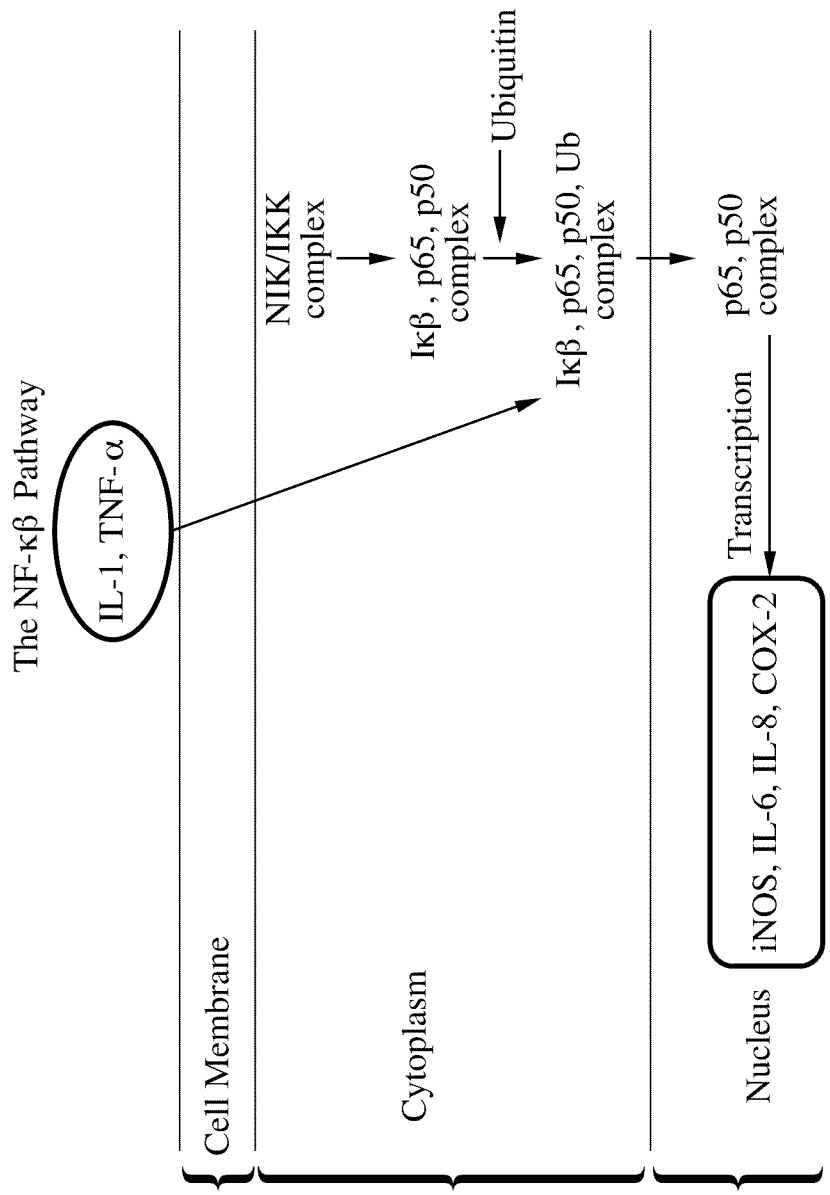

FIG. 7 shows a schematic view of a NF-κβ pathway associated with certain pain factors.

Figure 8:
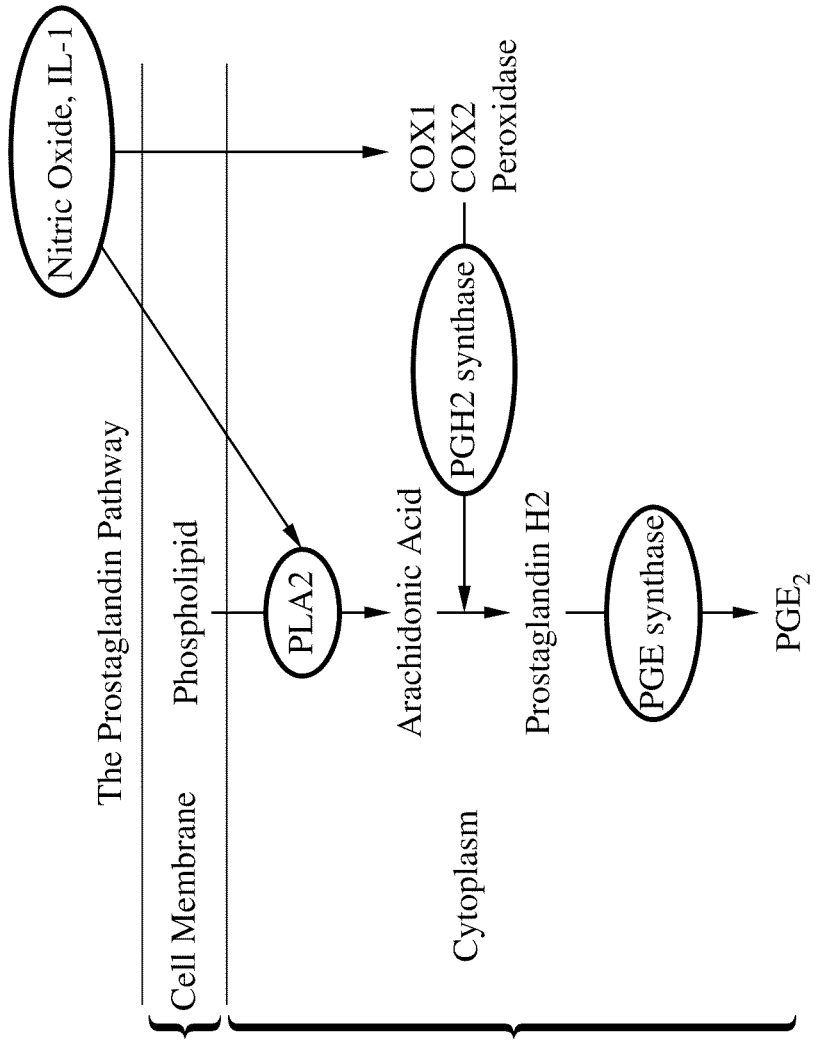

FIG. 8 shows a schematic view of a prostaglandin pathway associated with certain pain factors.

DETAILED DESCRIPTION OF THE INVENTION

Referring more specifically to the drawings, for illustrative purposes the present invention is embodied in the systems and methods generally shown in or illustrated by reference to FIG. 1 through FIG. 8. It will be appreciated that the apparatus may vary as to configuration and as to details of the parts, and that the method may vary as to the specific steps and sequence, without departing from the basic concepts as disclosed herein.

Label Disc Features Associated with Pain

Discogenic pain is generally believed to be a multifactoral phenomenon in many cases. In particular, three illustrative factors are summarized in varying levels of detail here as examples that are considered contributors in various ways to (or otherwise indicative of) the generation or transmission of discogenic pain. It is believed that these illustrative factors frequently act as a co-existent combination, often acting simultaneously. These types of factors are summarized as follows.

One such factor type relates to the presence of nociceptors. Normally, intervertebral discs are substantially avascular and only sparsely innervated at the outer margins of the disc annulus. These unmyelinated, substance P (SP) or calcitonin gene-related peptide (CGRP) containing fibers are typically unresponsive and termed silent nociceptors [Cavanaugh, 1996]. SP and CGRP are believed to be the sensory transmitters of nociceptive information. As degeneration proceeds, nerves can follow microvessels and grow deeper into discs, which may occur for example either peripherally or via the endplate. This nerve and vessel in-growth is facilitated by degeneration-related decreases in disc pressure and proteoglycan content.

A second such factor type is generally embodied by the need for the intradiscal nociceptors to be sensitized, and thus generally involves agents providing such sensitization. This can occur for example via cytokines, which are typically small, secreted proteins that mediate and regulate inflammation. Elevated levels of certain cytokines have been measured in human discs, and are associated with degeneration and pain. Such major cytokines have been observed to include interleukin-1, -6, and -8, tissue necrosis factor-alpha (TNF-α), macrophage migration inhibitory factor (MIF), and prostaglandin $E_2$ (PGE$_2$). The source of cytokines can be circulating inflammatory cells, such as for example in the case of herniated discs, or disc cells, such as for example in the case of contained disc degeneration. These pro-inflammatory stimuli can trigger cells to initiate a number of catabolic programs meant to stimulate tissue repair and remodeling that includes production of matrix metalloproteinases 1, 9 and 13. During this wound healing process, cytokines are also often involved in stimulating angiogenesis and granulation tissue formation.

In one particular beneficial embodiment of the present invention, cytokines and/or their cell-surface receptors are imaged at sites of inflammation in vivo using labeled markers, such as radiolabels. In particular beneficial examples, cytokines are tagged with one or more of the following, without limitation: iodine-123, iodine-125, iodine-131, technetium-99m, fluorine-18, or indium-111. In addition, positron-emitting radioisotopes (for example and without limitation fluorine-18) can be imaged using positron emission tomography (PET) or positron emission tomography-computed tomography (PET-CT). Other radiolabeled compounds can be imaged for example using single photon emission computerized tomography (SPECT).

It is also to be appreciated that MRI may be employed according to further embodiments for visualizing or observing accumulation or binding of various labeled markers variously herein described, such as for example in applying gadolinium as a marker tagged to or conjugated with certain labels to be bound to pain factors. Moreover, nanoparticles such as gold or iron oxide may be used as labels or markers to bind and thereafter be viewed or selectively targeted for therapy using appropriate visualization or treatment modalities, respectively.

A third such factor related to discogenic back pain involves disc depressurization that leads to mechanical instability while a pre-stress in the annulus and interspinal ligaments is diminished. Depressurization and instability, in turn, lead to abnormal internal disc stress that may stimulate nerves, leading to discogenic pain. Abnormal disc stress may also cause disc cells to be pro-inflammatory, compounding the adverse effects of an abnormal mechanical environment.

Labeling and Imaging Nerve Factors

According to certain particular embodiments, one or more materials associated with nerves in or around intervertebral discs are labeled with markers that are imaged for localization of pain. This is premised in part on the presence of certain such factors as indicators that pain may originate or transmit in the area. These embodiments include, without limitation, labeling structures or substances associated with nerves themselves. Further detailed modes of this include labeling substances within nerves, such as in particular but without limitation substance P or "CGRP". Other nerve fiber factors, substances or components that may be labeled according to such further embodiment(s) include, without limitation: TRK-α; anti-TRK-α antibody; nerve growth factor (NGF); anti-NGF antibody; NGF antagonist; anti-NGF antagonist antibody; PGP 9.5; SYN; peripherin; or other form of nerve antibodies or related materials in general. Other materials such as neurofilament 200 kD (NF200) [Johnson, 2001; Ashton, 1994] may also be the target of such labeling and subsequent imaging.

As apparent from these highly beneficial illustrative embodiments just noted immediately above (and elsewhere herein), endogenous substances such as TrkA or NGF may be targeted as the pain factor for labeling, or related antibodies or other substances having particular binding affinity or specificity to such resident materials may be bound to them in the area of pain and then thereafter provide the binding site for targeted labels to be subsequently delivered. In this regard, it is to be appreciated that various forms binding agents are broadly contemplated hereunder this description, though they may not be particularly antibodies affecting function of the target for binding. For example but without limitation, an antibody mimetic may be employed according to the present embodiments. Furthermore, various such substances described hereunder as targeted pain factors may be themselves labeled as markers and delivered to other targets. For example, NGF may be labeled and artificially delivered as the agent to mark TrkA as the targeted pain factor for imaging. In each of these different types of exemplary cases, the ultimate target for labeling via a separately delivered agent (e.g. whether the target is an endogenous resident substance or an artificially delivered substance) is considered a "nerve factor" as a pain factor according to the present embodiments.

The following description provides further understanding of the role of these types of chemicals and other materials with respect to these present embodiments. Further description of the benefits of various particular illustrative examples are also provided elsewhere herein for a further understanding.

The intervertebral disc is normally avascular and only sparsely innervated at the outer layers of the annulus fibrosus and the vertebral endplate [Fagan, 2003]. The outer ⅓ of the posterior annulus is believed to be most typically innervated by the afferent fibers from the sinovertebral nerve, which is considered a 'recurrent branch' of the ventral ramus of the spinal nerve at the same level [Nakamura, 1996]. The ventral and lateral aspects of the annulus are believed to be most typically innervated by the dorsal root ganglion (DRG) [Aoki, 2004]. Also, it has been reported that sensory fibers from upper level DRGs are believed to most typically innervate the dorsal portion of discs via the paravertebral sympathetic trunk [Ohtori, 2001].

The endplate is also suggested to be innervated by the basivertebral nerve, which as further suggested may be a branch of the sinovertebral nerve entering the vertebral body through the posterior neurovascular foramen [Antonacci, 1998].

Nerves usually accompany blood vessels, but can be found as isolated nerves in disc matrix. These non-vessel-associated fibers found in back pain patients have been observed to express growth-associated protein 43 (GAP43) as well as SP [Freemont, 1997]. Small disc neurons contain CGRP and also express the high-affinity nerve growth factor (NGF) receptor, tyrosine kinase A (trkA)[Aoki, 2004]. Disc inflammation has been observed to cause an increase in CGRP positive neurons [Aoki, 2004]. A recent study showed that NGF is expressed in microvascular blood vessels in a painful lumbar disc, and that there are trkA (TRK-α) expressing nerve fibers adjacent to the vessels that enter painful discs primarily through the endplate [Freemont, 2002; Brown, 1997]. Along with nerves growing into degenerated discs are specialized nerve support cells termed 'glia' or Schwann cells localized using glial fibrillary acidic protein (GFAP) [Johnson, 2001].

Accordingly, various such materials may provide the requisite binding affinity or specificity to painful regions (or highly innervated regions) to play the role as the labeled marker agent for delivery to pain factor targets. Or, these materials may provide the particular target as the pain factor to be labeled with selectively bound markers according to various embodiments of the present invention. In one particular beneficial example, TrkA antibody (or other binding agent) is labeled and delivered as a marker for binding and visualization at a location associated with pain. In another beneficial example, NGF itself is labeled and delivered as a marker to itself bind to TrkA. In further embodiments, the resident quantities of these materials are treated as the pain factors themselves for targeted labeling, e.g. using antibodies or other agents with beneficial binding affinity and/or specificity to these types of resident compounds in painful regions.

The following Published PCT Patent Applications are herein incorporated in their entirety by reference thereto: WO 2004/032870; WO 2004/058184; WO 2004/073653; WO 2004/096122; and WO 2005/000194.

The various compositions and methods described in these incorporated references may be adopted where appropriate to one of ordinary skill as label/marker vehicles and/or pain factor targets according to further embodiments of the various aspects and modes of the present invention herein described. For example without limitation, NGF antagonists, anti-NGF antibodies, anti-NGF antagonist antibodies, and various combinations or blends of these, or analog or derivatives thereof, may be so incorporated as further embodiments of the aspects herein described. Moreover, additional compounds may also be included in the agent delivery scheme, or as additional targets for labeled markers, such as for example opioids, NSAID, or other molecules or drug agents related to pain therapy.

Labeling and Imaging Blood Vessel Factors

Since blood vessels typically run along side and co-existent with nerves, factors related to blood vessels may also be labeled and imaged as indicia regarding vascularity itself, or as a measure of concomitant innervation in an area. Such constitutes a further embodiment contemplated hereunder, and described in some further detail as follows. In one regard, PECAM and/or CD34 [Freemont, 2002; Brown, 1997] may be appropriate targets as factors related to blood vessels and thus indicating their presence in a particular location or region. Another example of an appropriate target includes GFAP for endothelial cells [Johnson, 2001]. Other microvessel-related factors are considered as included, though not specifically listed here, as would be apparent to one of ordinary skill based upon review of this disclosure and other available information.

Labeling and Imaging Inflammatory Factors

According to still further embodiments contemplated hereunder, inflammatory factors themselves may be labeled with targeted markers and imaged as indicators of pain in a location or area. One exemplary type of such factor includes cytokines, such as for example but without limitation (though considered of particular benefit): tnf-α, or certain interleukins such as IL-1, 6, or 8 (or other interleukins). Another exemplary pro-inflammatory factor includes MIF and $PGE_2$.

Other factors considered indicative of certain activities or environmental considerations believed linked to pain, and thus appropriate targets for labeling and imaging using targeted markers, include: pH (e.g. in particular marking low pH as indicator of pain; or O2 levels, e.g. in particular marking low O2 as indicator of pain).

Cytokines, in the present context, are generally described as small, secreted proteins that mediate and regulate inflammation. They generally act over short distances, short times, and at very low concentrations. They typically function by binding to specific membrane receptors, which often then signal the cell via second messengers (discussed below) to alter gene expression. Responses to cytokines include increasing or decreasing expression of membrane proteins (including cytokine receptors), cell proliferation, and secretion of effector molecules. Cytokines may act on the cells that secrete them (autocrine action), on nearby cells (paracrine action), or in some instances on distance cells (endocrine action). It is common for different cells types to secrete the same cytokine or for a single cytokine to act on several different cell types (pleiotropy). Cytokines are redundant in their activity, and are often produced in a cascade, as one cytokine stimulates its target cells to make additional cytokines. Cytokines can also act synergistically or antagonistically.

Elevated levels of certain cytokines have been measured in human discs, and have been associated with degeneration and pain. Among the major cytokines found are, for example and without limitation: interleukin-1, -6, and -8, tissue necrosis factor-alpha (TNF-α), and prostaglandin $E_2$ ($PGE_2$)[Miyamoto, 2000; Ahn, 2002; Olmarker, 1998; Weiler, 2005]. The source of cytokines can be circulating inflammatory cells in the case of herniated discs [Kawaguchi, 2002; Woertgen, 2000], or disc cells in the case of contained disc degeneration [Burke, 2002].

Figure 1:
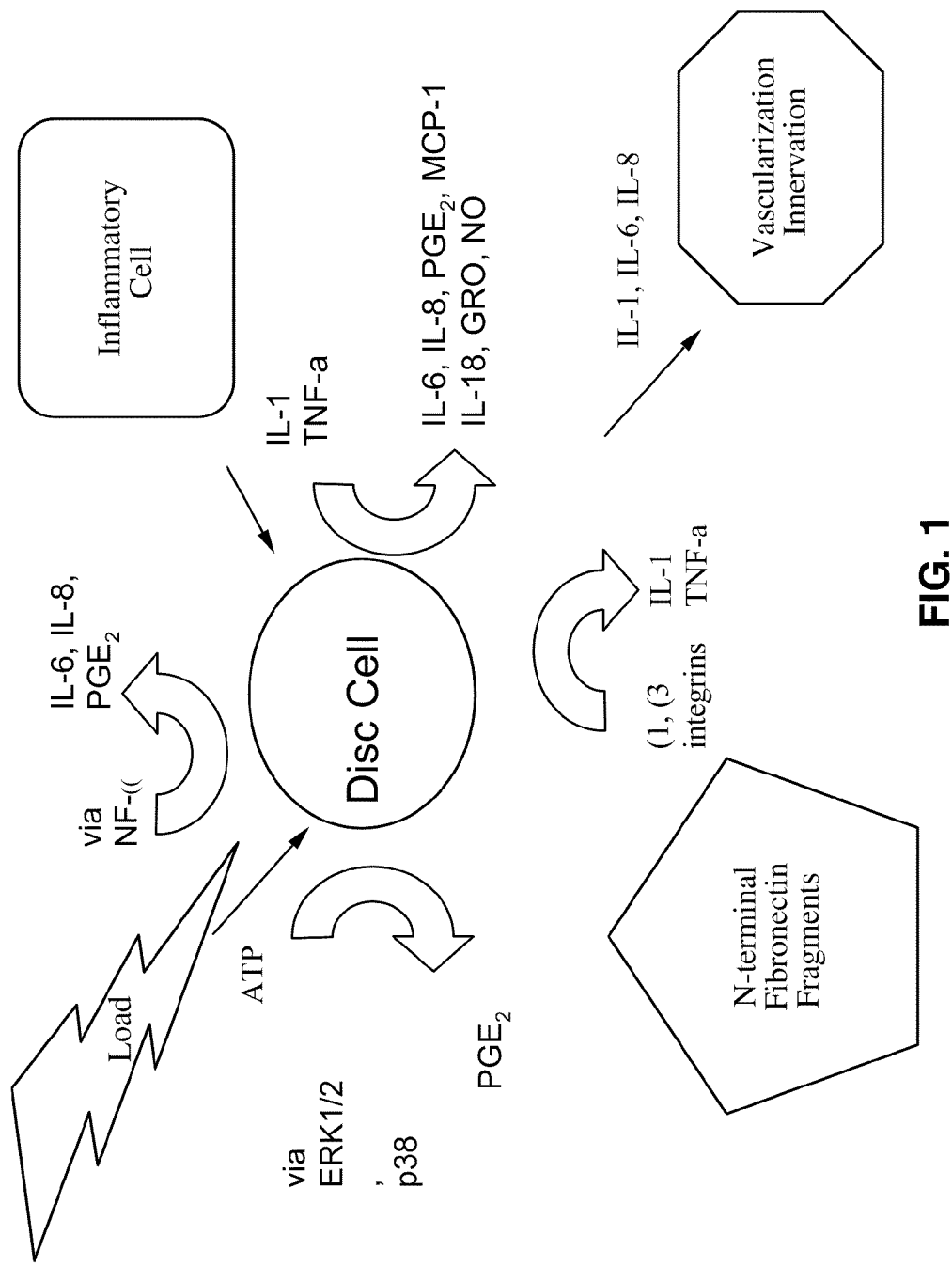
Figure 2A:
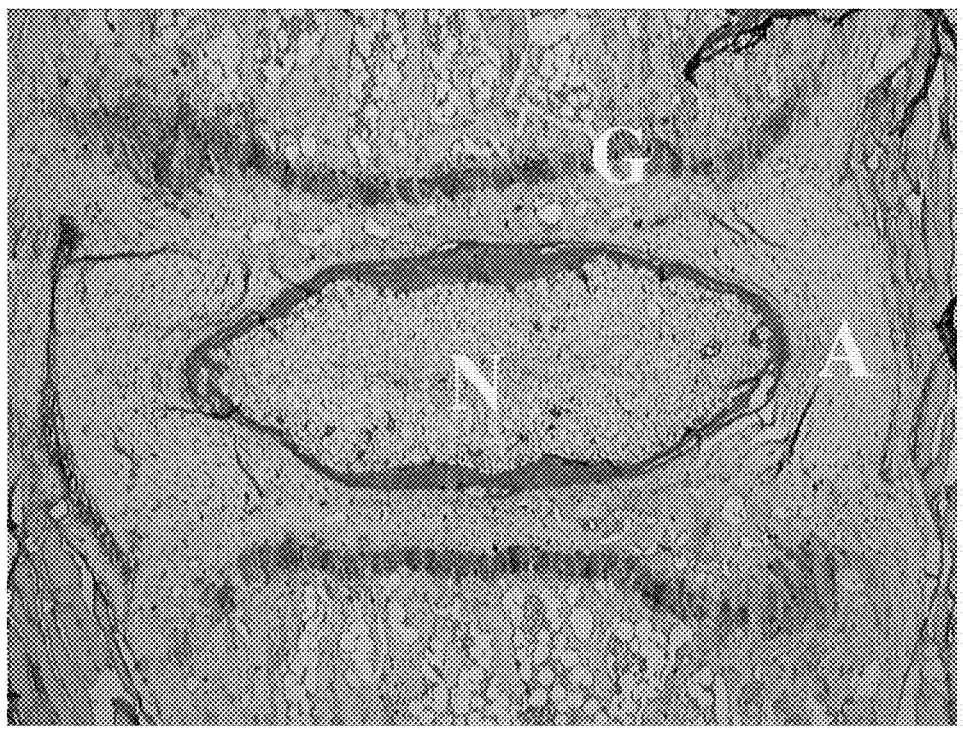
FIG. 2A shows a mid-sagittal section of normal mouse-tail disc demonstrating TNF-alpha localization in periphery of nucleus pulposus (brown stain).
Figure 2B:
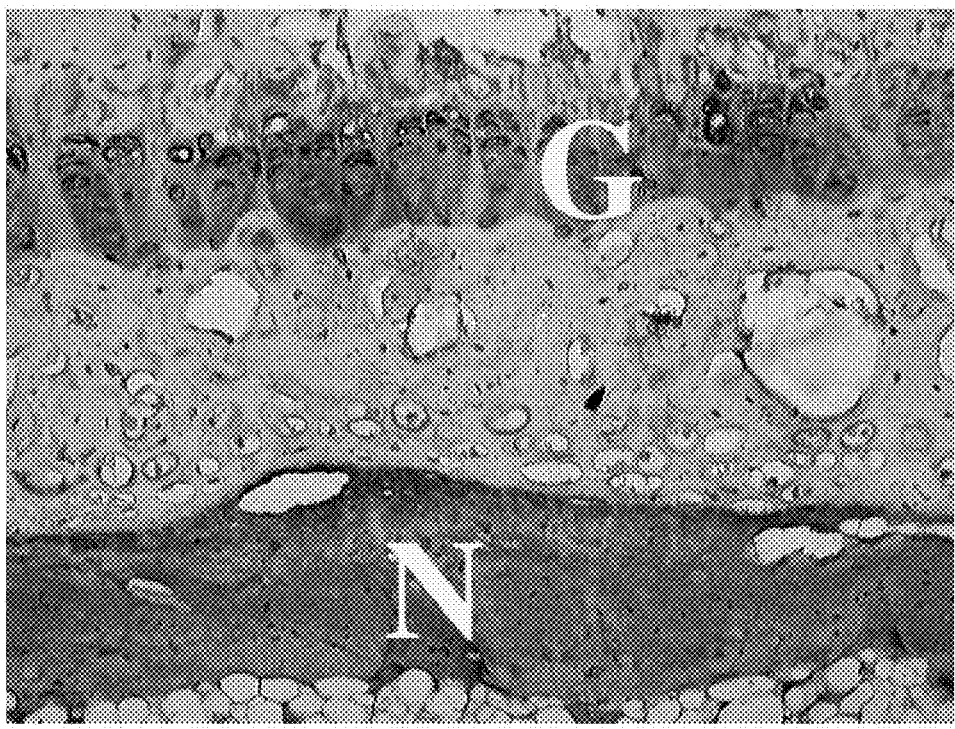
FIG. 2B shows a normal mouse disc wherein localization of TNF-alpha is present in the hypertrophic zone of the growth plate as generally expected.
Figure 2C:
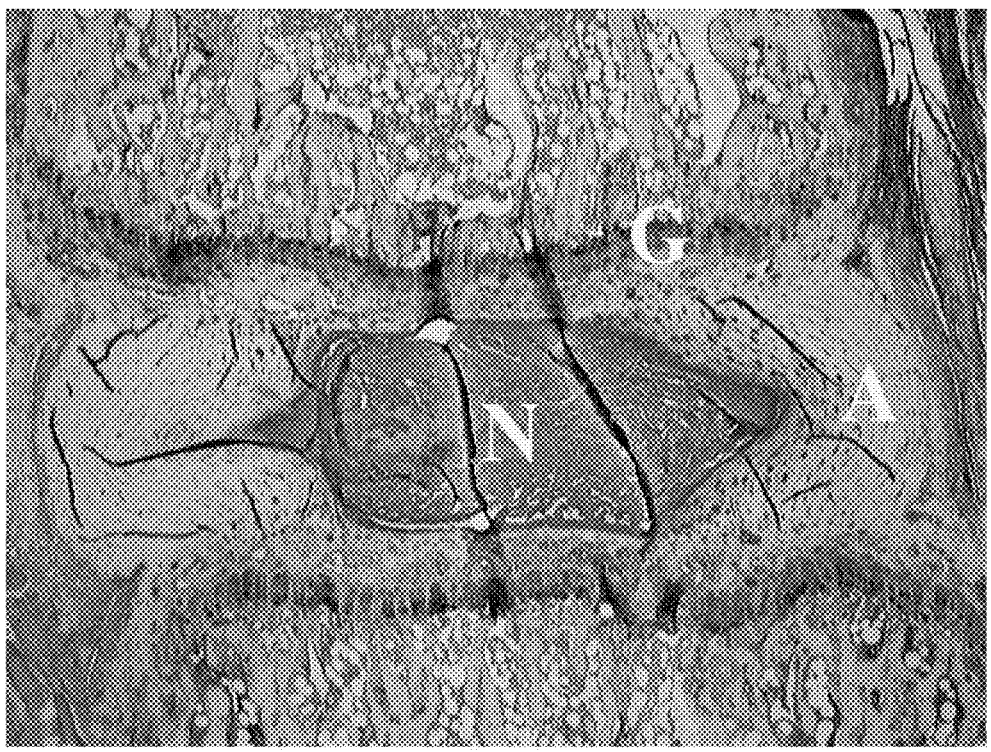
FIG. 2C shows in the compressed disc wherein increased amounts of TNF-alpha are apparent within the nucleus and inner annulus.
Figure 2D:
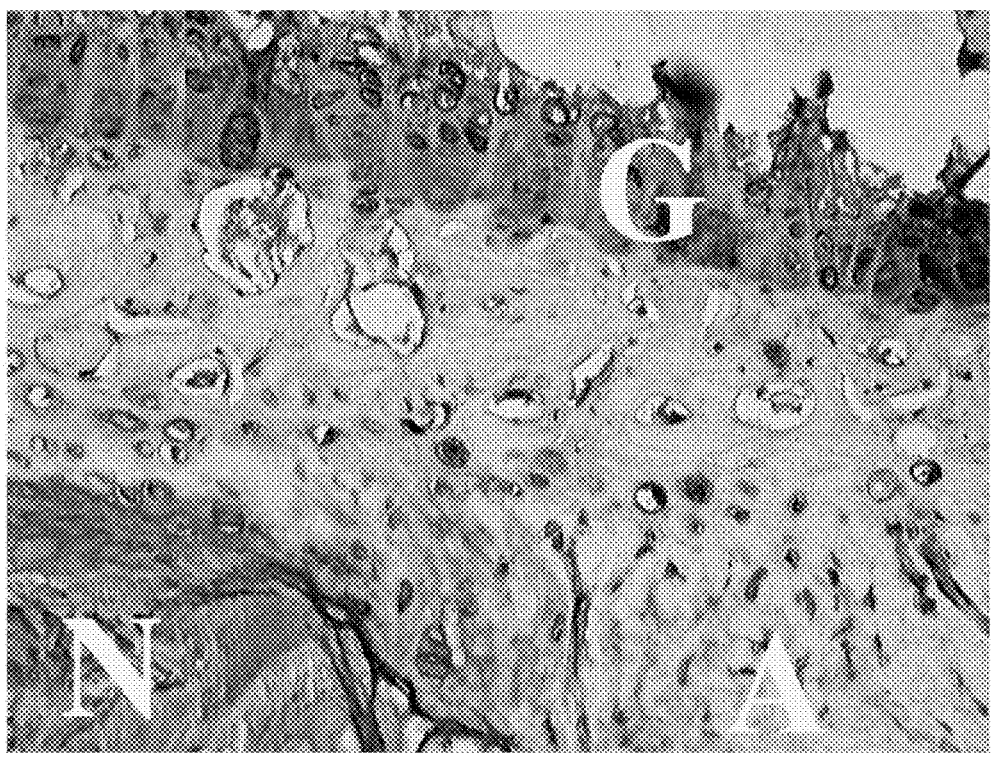
FIG. 2D shows increased TNF-alpha in the nucleus, inner annulus and irregularities in growth plate observed in compressed disc.

For disc cells, inflammatory factor production may be stimulated for example as part of several signaling cascades (described below), by fragments of degraded extracellular matrix, or matrix deformation (FIG. 1). These exemplary pro-inflammatory stimuli can trigger cells to initiate a number of catabolic programs meant to stimulate tissue repair and remodeling that includes production of matrix metalloproteinases 1, 9 and 13 [Anderson, 2002]. During this wound healing process, cytokines are also involved in stimulating angiogenesis and granulation tissue formation [Gillitzer, 2001].

IL-1 and TNF-α

IL-1b and TNF-α have been observed to demonstrate overlapping pro-inflammatory effects, activate common signaling cascades, and induce similar target genes (see ref in Faur). Effector cascades mediating inflammatory responses to IL-1 and TNF-α include the mitogen-activated protein kinases (MAPK), NF-κβ, and prostaglandin signal transduction pathways (shalom-barak). The signaling molecule nitric oxide may also form important component of the inflammatory cascade.

Imaging via labeling tissue necrosis factor-alpha (TNF-α) provides one particular beneficial example of marking for imaging a pro-inflammatory cytokine that can chemically hypersensitize the intervertebral disc and spinal nerve roots, thereby contributing to low back pain. Studies have been conducted that utilize immunohistochemistry to localize TNF-α in histologic sections of normal and degenerated mouse-tail discs. These studies suggest that the levels of TNF-α are increased after compression-induced degeneration of the intervertebral disc (FIGS. 2A-D).

To demonstrate a TNF-α based localization modality of the present invention, compositions and methods have been developed that label TNF-α antibodies with I-125 so that variations in TNF-α content can be imaged in vivo. An experiment was conducted to observe and confirm the beneficial use of this approach as follows. Mice such as mouse 30 shown in FIG. 3 were subjected to conditions that initiate tail-disc degeneration (FIG. 3), and were then injected intravenously with I-125 labeled TNF-α antibody. These animals were then imaged with a phosphor imaging plate, such as plate 50 shown in FIG. 4. Use of this composition and imaging methods demonstrated readily observed increased uptake in the regions of the injured discs, such as seen in image 60 in FIG. 5 wherein four injured tails are shown in 2-group sets on either side of a centrally located control tail in the image that was not injured though received similar labeled marker injection.

This particular experiment was performed using a particular radio-labeled TNF-α blocker, more specifically infliximab (Trade name "Remicade™" commercially available from Johnson & Johnson), and demonstrates one exemplary embodiment adapted for beneficial use according to the present invention. While this particular modality is considered highly beneficial in the specific mode described, it is also exemplary of a number of broad aspects of the present invention that may be illustrated by many alternative or combinatorial approaches that are herein contemplated.

In one regard, the present illustrative embodiment provides an example of using a therapeutic compound that actually provides some pain-related therapy (e.g. TNF-α antibody or other form of blocker) that is also used to image the location of the pain being treated (as the labeled marker, as conducted in the illustrative experiment, or targeted factor itself). This step may be followed by additionally treating the imaged region thereafter with additional spacially localized or directed therapies. Examples include, without limitation, directed energy therapies such as those elsewhere herein described, or further localized injection of similar or other therapeutic compound(s)).

In another more specific regard, TNF-α blockers or antibodies are contemplated as a class of therapeutic compounds beneficially adapted for use according to the invention, within which infliximab or Remicade™ (or analogs or derivatives thereof) is used in a particular beneficial embodiment as just described. These provide the benefit of selective uptake at nerve endings where pain may be occurring, and thus a particular beneficial target agent for labeling to image pain. They also provide the benefit of some therapeutic value to the pain itself.

Furthermore, it is to be appreciated that targeted agents, such as antibodies as herein described by way of example, may provide the label for imaging, or may take the form of the targeted factor (either by itself or by virtue of its conjugation or binding with a first resident factor). In the later case, delivery of the first factor is then subjected to subsequent labeling by delivery of a second agent as the labeled marker (again either by its imagability itself or as bound, associated, or conjugated with the first delivered agent to the region imaged).

MAPK Pathway

MAPKs form an intracellular signaling pathway built upon a self-propagating phosphorylation system (FIG. 6). Activation of MAPKs are one of the pivotal intracellular pathways triggered by cytokine receptors (Shalom-berak). Three MAPK subgroups have been identified: extracellular signal regulated kinase (ERK); the Jun $NH_2$-terminal kinases (JNK); and p38 (geng, others). In chondrocytes, ERK activation occurs in response to diverse stimuli, while JNK and p38 is only seen in response to IL-1 and TNF-α (Firestein, liancini): this signaling pathway is thought responsible for cartilage degradation (geng). JNK and p38 are collectively termed stress activated protein kinases (SAPKs). The signal is initiated by membrane-proximal small GTPases of the Rho family, activation of MLK, and phosphorylation and activation of MKK3/6 that in turn phosphorylates and activates p38. Faur).

One important endpoint of MAPK activation is the production of the phosphorylated active activator protein 1 (AP-1) transcription factor (heterodimer of c-Jun and c-Fos), which in turn, can influence chondrocyte collagenase activity (mengshol, Ferreria refs). AP-1 plays a central role in the transcriptional regulation of many MMP genes including collagenase and stromelysin (mengshol refs, Firestein). Similarly, MIF activates the MAPK pathway and AP-1 leading to cell proliferation, and $PGE_2$ production, which eventually promotes monocyte/macrophage activation. Certain published data suggests that MIF is in particular upregulated under conditions of chronic emotional stress and can potentiate elevated levels of other inflammatory factors such as for example those examples herein described. Accordingly, labeling MIF provides yet a further embodiment of the various present aspects.

JNK and p38 are essential for IL-1 induction of mmp-13, while ERK pathway is not. p38 is essential for multiple inflammatory genes, including Il-1, TNF-α, Il-6, stromelysin-1 (mmp-3) and mmp-1 (mengeshol).

It is to be appreciated that various such materials associated with pathways or molecular cascades associated with pain may provide the target for labeled markers and subsequent imaging as herein described, and various such materials are provided here as beneficial examples which, though of particular value, are also not intended to limit broad aspects contemplated hereunder. In addition, such otherwise indigenous materials may also demonstrate selective uptake in tissues associated with pain. In such case, these otherwise indigenous materials (or synthetic or other biologic constructs similar to them, such as analogs or derivatives thereof) may also be harnessed and labeled for delivery as the labeled marker. Moreover, due to their selective uptake, particular accumulated concentrations of certain molecules in areas of pain also render them viable targets as the pain factors themselves for labeling with labeled markers that bind to them.

NF-κβ Pathway

In addition to the MAPK induction, IL-1 and TNF-α activate NF-κβ. NF-κβ is a transcription factor that exists in a latent form in the cytoplasm of unstimulated cells and is composed of a transcriptionally active dimer (p65 and p50) bound to an inhibitor protein (Iκβ) (Bowie, Magnani). NF-κβ is activated by a large number of different signals that include similar cell stress signals that activate SAPKs. IL-1 and TNF-α trigger the phosphorylation and degradation of Iκβ, resulting in the release of NF-κβ to enter the nucleus (refs in Shalom; Baeuerle). NF-κβ activation occurs through a cascade starting with NF-κβ-inducing kinase (NIK), which then phosphorylates and activates the inhibitor of NF-κβ (Iκβ) kinases. Phosphorylation of Iκβ results in ubiquitination and degradation of Iκβ inhibitory subunit, allowing NF-κβ to translocate to the nucleus where it acts as a transcription factor and regulates its target genes, which include collagenase (MMP-1; Barchowsky) (Mengshol, magnani) and COX-2 (Mifflin). FIG. 7 shows certain further details of this cascade and relationship between components.

Prostaglandin Pathway

Eicosanoids are signaling molecules that act in an autocrine fashion. Pro-inflammatory stimuli can lead to increased phospholipid-derived eicosanoid synthesis that involves a cascade of three enzyme reactions (FIG. 8). First, arachidonic acid (AA) is liberated from its phospholipid storage sites by phospholipase A2 (PLA2). The next rate-limiting step is conversion of AA to prostaglandin H2 by cyclooxygenase (COX).

The prostaglandin pathway is stimulated by IL-1 b. This cytokine increases the activity of PLA2 and induces COX-2 gene expression by binding to a specific cell-surface receptor (IL-1 RI) that ultimately leads to increases in COX-2 promoter activity via the NF-κβ pathway (Faur refs, geng). In chondrocytes, COX activity is not increased by TNF-α. Rather, TNF-a can amplify COX activity in IL-1 stimulated cells. (Berenbaum).

Prostaglandin $E_2$ ($PGE_2$) stimulates the catabolism of chondrocytes, having both anti-proliferative and pro-apoptotic effects (berenbaum ref, also goldring ref in liancici). An increase in $PGE_2$ may therefore tip the balance toward catabolism.

Nitric Oxide

Nitric oxide (NO) is a small signaling molecule that is part of the catabolic program in chondrocytes induced by IL-1 and TNF-α (Lotz; Goldring). It is produced within the cell by the inducible isoform of NO synthase (iNOS), and then passes readily through the cell membrane to affect neighboring cells. Because it has a short half-life (5 to 10 seconds) it acts only locally, yet it plays an important role in the pathophysiology of arthritic disease (Ferreira Mendes). It has been shown to: induce apoptosis (by stimulating release of cytochrome c from mitochondria) and inflammation (by activating COX and PLA2 (Vassalle, clancey)); suppress collagen and proteoglycan synthesis; and upregulate MMP synthesis (Scheurwegh).

IL-1 and TNF-α increase the gene expression and synthesis of iNOS, through the transcription factors NF-κβ and AP-1. Activation of NF-κβ is an essential step for iNOS induction (see Mendes refs). Also, there is some evidence that the MAPK p38 may be involved in the activation of NF-κβ and subsequent iNOS expression, since p38 is reported to be required for IL-1-induced iNOS expression in chondrocytes (Mendes).

Labeling/Imaging Cellular Factors Associated with Inflammation

Cells that produce or are associated with inflammatory factors can also be labeled with targeted markers and thereafter imaged as an indicator that pain exists in the area. For example, disc cells that are actively synthesizing inflammatory factors may be labeled as such (or components thereof may be labeled). Inflammatory cells that are attracted to painful discs, such as for example leukocytes, may be labeled and imaged for this purpose.

The following articles are herein incorporated in their entirety by reference thereto.

1. Haro H, Crawford, H. J. Clin. Invest. 2000; 105:143-150.
2. Mow V, Hayes, W. Basic Orthopaedic Biomechanics. In. New York: Raven Press, 1991; 339-342.
3. Thompson J P, Pearce, R. H., Schechter, M. T., Adams, M. E., Tsang, I. K., Bishop, P. B. Preliminary evaluation of a scheme for grading the gross morphology of the human intervertebral disc. Spine 1990; 15:411-415.
4. Iatridis J C, Setton, L. A., Weidenbaum, M., Mow, V. C. Alterations in the mechanical behavior of the human lumbar nucleus pulposus with degeneration and aging. In: Journal of orthopaedic research, 1997; 318-322.
5. Urban J P, McMullin, J. F. Swelling pressure of the intervertebral disc: influence of proteoglycan and collagen contents. Biorheology 1985; 1985.
6. Beall P T, Amety, S. R. et al. States of Water in Biology: NMR Data Handbook for Biomedical Applications. New York: Pergamon Press, 1984.
7. Boos N, Boesch, C. Quantitative magnetic resonance imaging of the lumbar spine: potential for investigations of water content and biochemical composition. Spine 1995: 2358-2366.
8. Bottomley P A, Foster, T. H. et al. A review of normal tissue hydrogen NMR relaxation times and relaxation mechanisms from 1-100 MHz: dependence on tissue type, NMR frequency, temperature, species, excision, and age. Medical Physics 1984: 425-448.
9. Lyons G, Eisenstein, S. M. et al. Biochemical changes in intervertebral disc degeneration. Biochim Biophys Acta 1981: 443-453.
10. Majors A W, McDevitt, C. A. et al. A correlative analysis of T2, ADC and MT ratios with water, hydroxyproline and GAG content in excised human intervertebral disk. In: 40th Annual Meeting Orthopaedic Research Society. New Orleans, La.: Orthopaedic Research Society, 1994.
11. Maroudas A. The Biology of the Intervertebral Disc. In: Ghosh P, ed. The Biology of the Intervertebral Disc. Boca Raton: CRC Press, 1988; Ch. 9.
12. Pearce R H, Grimmer, B. J. et al. Degeneration and the chemical composition of the human lumbar intervertebral disc. Journal of orthopaedic research 1987: 198-205.
13. Tertti M, Paajanen, H. et al. Disc degeneration in magnetic resonance imaging: a comparative biochemical, histologic, and radiologic study in cadaver spines. Spine 1991: 629-634.
14. Chui E, David C. Newitt, Mark R. Segal, Serena S. Hu, Jeffrey C. Lotz, Sharmila Majumdar. Magnetic Resonance Imaging Measurement of Relaxation and Water Diffusion in the Human Lumbar Intervertebral Disc Under Compression In Vitro. Spine 2001; 26:E437-444.
15. Gundry C R, Fritts, H. M. Magnetic resonance imaging of the musculoskeletal system: Part 8. The spine. Clin Orthop Rel Res 1997: 275-287.
16. Gunzburg R P Rea. A cadaveric study comparing discography, magnetic resonance imaging, histology and mechanical behavior of the human lumbar disc. Spine 1991: 417-423.
17. Modic M T, Pavlicek, W. et al. Magnetic resonance imaging of intervertebral disc disease: clinical and pulse sequence considerations. Radiology 1984: 103-111.
18. Modic M T, Masaryk, T. J. et al. Lumbar herniated disk disease and canal stenosis: prospective evaluation by surface coil MR, CT and myelography. ANJR 1986: 709-717.
19. Modic M T, Masaryk, T. J. et al. Imaging of degenerative disc disease. Radiology 1988: 177-186.
20. Sether L A, Yu, S. et al. Intervertebral disk: Normal age-related changes in MR signal intensity. Radiology 1990: 385-388.
21. Pfirrmann C, Metzdorf, A., Zanetti, M. Magnetic Resonance Classification of Lumbar Intervertebral Disc Degeneration. Spine 2001; 26:1873-1878.
22. Nieminen M T, Rieppo, J., Silvennoinen, J. et al. Spatial assessment of articular cartilage proteoglycans with Gd-DTPA-enhanced T1 imaging. Magnetic Resonance in Medicine 2002; 48:640-648.
23. Mosher T J, Dardzinski, B. J., Smith, M. B. Human articular cartilage: influence of aging and early symptomatic degeneration on the spatial variation of T2-preliminary findings at 3 T. Radiology 2000; 214:259-266.
24. Boos N, Wallin, A., Boesch, C. H., Aebi, M. Quantitative MR Imaging of diurnal water content variations in lumbar intervertebral disc. In: 38th Annual Meeting, Orthopeadic Research Society. Washington, D.C.: The Orthopaedic Research Society, 1992; 165.
25. Boos N, Wallin, A., Harms, S., Vock, P., Boesch, C. H., Aebi, M. Tissue characterization of normal and herniated lumbar intervertebral discs by quantitative MRI. In: 39th Annual Meeting, Orthopaedic Research Society. San Francisco, Calif.: Orthopaedic Research Society, 1993; 417.
26. Burstein D, Gray, M. L. et al. Diffusion of small solutes in cartilage as measured by nuclear magnetic resonance (NMR) spectroscopy and imaging. Journal of orthopaedic research 1993: 465-478.
27. Koh K, Kusaka, Y. et al. Self diffusion coefficient of water and its anisotropic property in bovine intervertebral discs analyzed by pulsed gradient NMR method. Orthop Trans 1992: 483.
28. Koh K, Kusaka, Y. et al. Self diffusion coefficient of water in human intervertebral discs analyzed by pulsed gradient NMR method. In: 39th Annual Meeting Orthopaedic Research Society. San Francisco, Calif., 1993.
29. Abdulkarim J A, Dhingsa, R., Finlay, D. B. Magnetic Resonance Imaging of the Cervical Spine: Frequency of Degenerative Changes in the Intervertebral Disc with Relation to Age. Clinical Radiology 2003: 980-984.
30. Swanson M G, Vigneron D B, Tabatabai Z L, et al. Proton HR-MAS spectroscopy and quantitative pathologic analysis of MRI/3D-MRSI-targeted postsurgical prostate tissues. Magnetic Resonance in Medicine 2003; 50:944-954.
31. Schiller J, Naji, L., Huster, D., Kaufmann, J., Arnold, K. 1H and 13C HR-MAS NMR investigations on native and enzymatically digested bovine nasal cartilage. Magnetic Resonance Materials in Physics, Biology and Medicine 2001: 19-27.
32. Carr H Y, Purcell, E. M. Effects of Diffusion on Free Precession in Nuclear Magnetic Resonance Experiments. Physical Review 1954; 94:630-638.
33. Kupce E. Applications of adiabatic pulses in biomolecular nuclear magnetic resonance. In: Methods in Enzymology, 2001; 82-111.
34. Mucci A, Schenetti, L., Volpi, N. 1H and 13C nuclear magnetic resonance identification and characterization of components of chondroitin sulfates of various origin. Carbohydrate Polymers 2000: 37-45.
35. Goupille P, Jayson, M. I., Valat, J. P., Freemont, A. J. Matrix metalloproteinases: the clue to intervertebral disc degeneration? Spine 1998; 23:1612-1626.
36. Kang J D, Stefanovic-Racic, M., McIntyre, L. A., Georgescu, H. I., Evans, C. H. Toward a biochemical understanding of human intervertebral disc degeneration and herniation. Contributions of nitric oxide, interleukins, prostaglandin E2, and matrix metalloproteinases. Spine 1997; 22:1065-1073.
37. Weiler C, Nerlich, A. G., Zipperer, J., Bachmeier, B. E., Boos, N. 2002 SSE Award Competition in Basic Science: Expression of major matrix metalloproteinases is associated with intervertebral disc degradation and resorption. European Spine Journal 2002: 308-320.
38. Urban J P, Roberts, S., Ralphs, J. R. The Nucleus of the Intervertebral Disc from Development to Degeneration. In: American Zoologist, 2000; 53-61.
39. Weidenbaum M, Foster, R. J., Best, B. A., Saed-Nejad, F., Nickoloff, E., Newhouse, J., Ratcliffe, A., Mow, V. C. Correlating magnetic resonance imaging with the biochemical content of the normal human intervertebral disc. Journal of orthopaedic research 1992; 10:552.
40. El-Sayed, I. H., Huang, X., El-Sayed, M. A. "Surface Plasmon Resonance Scattering and Absorption of anti-EGFR Antibody Conjugated Gold Nanoparticles in Cancer Diagnostics: Applications in Oral Cancer," Nano Letters 2005 Vol. 5 No. 5 829-834.
41. Herold, D. M., Das, I. J., Stobbe, C. C., Iyer, R. V., Chapman, J. D., "Gold microspheres: a selective technique for producing biologically effective dose enhancement," Int. J. Radiat. Biol. 2000, Vol. 76, No. 10, 1357-1364.

It is to be appreciated based upon the foregoing disclosure that pain factors are labeled and imaged in order to identify, with a useful degree of geographic specificity, active pain sites in and around skeletal joints. Such is considered highly beneficial in particular for use in diagnosing the cause of pain, and understanding where and how to treat for pain relief, such as for example with local ablation or energy delivery systems, and/or local drug delivery.

Various terms have been used herein of a certain technical nature, and should be given their standard technical meaning in the context of the particular art to which this disclosure pertains, and in the context of their use in this description together with other accompanying disclosure, unless otherwise given a specific meaning hereunder. Notwithstanding the foregoing, it is understood that certain specific materials or types of materials are identified, whereas other similar materials or types of materials are also intended to be implicated within the broad scope intended for the current invention. For example, "pain factors" are herein identified as playing a role in various of the present embodiments. Such terms are intended to mean any and all materials, whether structural, chemical, or otherwise, that have an association, either directly or indirectly, with pain such that binding them provides a vehicle to enhance diagnosis or therapy in relation to the associated pain. In one particular example, factors related to transmitting pain signals along or between nerves are to be included. Or, factors that stimulate pain, such as "inflammatory" materials, are indicated. Materials related to other points in a chemical or biological cascade related to pain are also implicated, such as factors that relate to secondary or tertiary products or components of such pain generation or transmission process. If a factor is distinctly present (or absent) in a somewhat recognizable manner when and where pain is present, and in a different level or manner than when and where pain is not present, then it is considered a "pain factor" as herein described. This use of the term "factor" similarly applies in other contexts herein provided, such as for example "inflammatory factors", "cellular factor(s)", "nerve factors", etc.

In another regard, it is also contemplated that, where certain specific examples of chemicals or materials are herein provided, other related compounds may be interposed in addition or in the alternative to such specified compound. For example, agents related to a certain material may be suitable substitutes and may include for example precursor materials, such as a material that may be metabolized or otherwise altered to produce the specified "factor" or "label" or other compound or material referenced. Analogs or derivatives of the specified material may also be suitable in similar uses or preparations or systems. This includes for example modified molecular forms of a specified material that retain the related binding or other activity of the specified material so as to perform as herein described as a labeled pain factor or targeted label.

Moreover, use of a "marker" or "label" to tag or label a "factor" is generally herein described in fairly simple terms for the purpose of providing a general overall understanding of the broad aspects contemplated hereunder. However, the actual steps and/or materials used in order to achieve such "labeled pain factor" result may be more extensive than herein described, though may be carried out by one of ordinary skilled in the art based upon review of this disclosure in its entirety in combination with other available related information and thus further contemplated hereunder. For example, intermediary tagging, labeling, or binding may be beneficially used in order to achieve the labeled marking necessary to provide differential imaging of the labeled result in a useful manner.

In one further exemplary embodiment, bi-specific antibodies maybe used in such a manner as follows. One binding site of the bi-specific antibody provides a particular binding affinity for the pain factor being targeted, and thus differentially binds to that factor. However, this is done in a manner leaving a second binding site exposed, and which second binding site has binding specificity to a second material as a label agent. This second material thereafter binds to the second binding site of the bi-specific antibody bound at the first site to the pain marker. The result provides a labeled marker on the pain factor via the second material, which is tagged to the pain factor via use of this intermediary bi-specific antibody.

It is also to be understood that the labeled marking of pain factors herein described is of particular benefit with respect to thereafter image the result. While imaging the "labeled pain factor" may be generally described, it is to be understood that what is imaged by the particular imaging modality may include without limitation: the overall conjugate or combination of label-plus-factor; the label itself; the factor itself (e.g. to the extent modified in a recognizable way by the labeled marking); or combinations of the above, including in further modes use of intermediary binding materials such as for example bi-specific antibodies as herein described.

One particular example of a labeled marker and pain factor combination believed to be useful according to certain of the embodiments herein described is provided in finer detail to provide a further understanding. This relates to radiolabeled TNF-α antibodies and related imaging tools herein described. However, it is to be appreciated that this approach, though in particular highly beneficial, is exemplary of broader aspects of the present invention and other labeling and/or marker modalities, or targeted vehicles such as without limitation antibodies, and/or imaging tools are contemplated and may be used without departing from the intended broad scope according to various aspects of the invention.

The invention according to further aspects provides a unique ability to direct therapy to pain, including without limitation pain associated with musculoskeletal joints and in particular the spine. Accordingly, the systems and methods of the invention according to further embodiments also include therapeutic device assemblies for delivering such therapy. Such may include local drug or other chemical delivery modalities. Or, therapeutic dosing of energy may be delivered, such as for example radiofrequency (RF) energy delivery probes, ultrasound probes, high intensity focused ultrasound (HIFU), light energy (e.g. lasers for example), microwave energy, or cryovascular therapeutic tools may be used. By identifying where treatment is required due to the selectively visualized pain factors there, these tools may be used in a more efficient manner. Accordingly, the compositions of labeled markers, the visualization or imaging tools, and the therapeutic tools are thus used in an overall symphony that together provides beneficial healthcare results in treating pain.

This is in particular the case with respect to back pain. For example, a disc may be identified as a source of pain, whereas lack of further clarity may render it difficult to treat the pain in a selective way. Often, ablation of the entire disc is not desired. According to certain further embodiments, the labeled marking of pain factors and related imaging is used to identify more specifically where pain occurs. In one mode, at least one-half of the disc is identified as the target for therapy. In another mode, the labeled marker visualization localizes the target for therapy to one or more quarter quadrants of the disc. In still further embodiments, directionally localized energy delivery, e.g. laser, ultrasound, or microwave, may be particularly beneficial for isolating the therapy to the isolated region of visualized, labeled pain factors. Furthermore, local injections of pain medication may be directed via such targeted labeling and related imaging of pain localization.

In another highly beneficial aspect, pain factors that are visualized with targeted markers as described hereunder may relate to nerves that are located at least in part within bones. This may be the case for example with respect to bony endplates that are innervated with nociceptive nerve fibers. In one particular beneficial embodiment, pain factor imaging as herein described is used to locally identify one or more particular end-plates of vertebral bodies as the pain source. Accordingly in many such instances, a basivertebral ablation tool set and method may be used to ablate the basivertebral nerve that innervates that end-plate. This may be done for example using a mono- or bi-polar electrode assembly that is delivered via one or more needle or drill probes into the vertebral body that is used to RF ablate the nerve closer to a root trunk section within the bone. Despite this particular beneficial combination of tools and methods for treating pain in a uniquely localized manner, however, it is to be appreciated that other localized pain sources may be selectively visualized using a variety of useful targeted markers, and a variety of tools or methods may be used to direct therapy accordingly, without departing from the present intended scope of the present invention.

The following U.S. Patents are herein incorporated in their entirety by reference thereto: U.S. Pat. No. 5,391,197 to Burdette et al.; U.S. Pat. No. 6,074,352 to Hynynen et al.; U.S. Pat. No. 6,126,682 to Sharkey et al.; U.S. Pat. No. 6,231,528 to Kaufman et al.; U.S. Pat. No. 6,368,292 to Ogden et al.; U.S. Pat. No. 6,470,220 to Kraus, Jr. et al.; U.S. Pat. No. 6,562,033 to Shah et al.; U.S. Pat. No. 6,575,969 to Rittman III et al.; U.S. Pat. No. 6,699,242 to Heggeness; U.S. Pat. No. 6,736,835 to Pellegrino et al.; U.S. Pat. No. 6,827,716 to Ryan et al.; U.S. Pat. No. 6,907,884 to Pellegrino et al. The following published PCT Patent Applications are herein incorporated in their entirety by reference thereto: WO 2003/059437 to Diederich et al.; and WO 03/061756 to Diederich et al. The following Published US Patent Applications are also herein incorporate in their entirety by reference thereto: US 2004/0064137 to Pellegrino et al.; and US 2004/0064136 to Papineau et al.

Various different modes of "imaging" and related tools are herein contemplated, as apparent to one of ordinary skill to match the targeted marker modalities employed to accomplish the general objectives hereunder. In one regard, a variety of diagnostic tools may be used to acquire information related to the targeted pain factor(s) and related spacial location relative to surrounding tissues. This information may be processed and converted into a representation that may be displayed or otherwise conveyed to a healthcare provider in a manner sufficient and useful to understand the spacial location of the associated pain. Accordingly, various different types of sensors, data acquisition systems, processors, and displays may be used in various combinations to convert the labeled marking to useful information to such healthcare providers. Many of these are commercially available in sufficient form to readily integrate with the targeted marker agents and delivery systems herein described (which may further include therapeutic aspects) in an overall system sufficient to provide useful information in medical patient management.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A method for conducting a medical procedure on intervertebral discs of a spine in a body of a discogenic back pain patient, comprising:
   providing a substantially targeted agent that is adapted to differentially bind to a pain factor;
   conjugating the targeted agent with an imaging contrast label to thereby form a targeted label configured to label the pain factor via the bound pain factor-label conjugate;
   locally injecting into a first disc, using a local injection assembly, the targeted label in a manner that is adapted to differentially bind to and label the pain factor in a first region of tissue at a first location in the first disc;
   locally injecting into a second disc, using a local injection assembly, the targeted label in a manner that is adapted to differentially bind to and label the pain factor in a second region of tissue at a second location in the second disc;
   binding the pain factor at the first and second locations with the injected targeted label, thereby artificially labeling the pain factor with the targeted label at the first and second locations in a manner substantially increasing the ability to image the pain factor with an imaging tool;
   imaging the first and second discs with the imaging tool in a manner sufficient to selectively differentiate a first concentration of the labeled pain factor in the first region of tissue at the first location relative to a second concentration of the labeled pain factor in the second region of tissue at the second location;
   wherein imaging the labeled pain factor comprises using the imaging tool to image the label coupled to the pain factor via the bound targeted agent, and the first and second concentrations are a function of the amounts of the label at the first and second locations;
   wherein the pain factor comprises a nerve factor;
   wherein the nerve factor comprises receptor tyrosine kinase A (trkA);
   wherein the targeted agent comprises a trkA binding agent or antibody; and
   diagnosing the first and second locations as relatively painful versus non-painful by comparing the selectively differentiated first and second concentrations.

2. The method of claim 1, wherein the targeted agent comprises nerve growth factor (NGF).

3. The method of claim 1, wherein the imaging contrast label used to conjugate the targeted agent comprises a nanoparticle.

4. The method of claim 1, wherein the imaging contrast label used to conjugate the targeted agent comprises at least one of gold or iron oxide.

5. The method of claim 1, wherein imaging contrast label used to conjugate the targeted agent comprises a magnetic resonance imaging (MRI) contrast agent.

6. The method of claim 5, wherein the MRI contrast agent comprises gadolinium.

7. The method of claim 5, wherein imaging the labeled pain factor comprises:
using an MRI scanner to image the MRI contrast agent coupled to the pain factor via the bound targeted agent.

8. The method of claim 1, wherein the imaging contrast label comprises an ultrasound contrast agent.

9. The method of claim 8, wherein imaging the labeled pain factor comprises:
ultrasonically imaging the ultrasound contrast agent label coupled to the pain factor via the targeted agent.

10. The method of claim 1, wherein the imaging contrast label used to conjugate the targeted agent comprises a radiographic contrast agent.

11. The method of claim 10, wherein imaging the labeled pain factor comprises:
X-ray imaging the radiographic contrast agent coupled to the pain factor via the bound targeted agent.

12. The method of claim 1, wherein the first region of tissue comprises only a portion that is less than all of the first intervertebral disc.

13. The method of claim 12, wherein the portion is less than or equal to about one-half of the first intervertebral disc.

14. The method of claim 13, wherein the portion is located within less than or equal to an about one-hundred eighty degree angular circumferential region of the first disc in a transverse plane relative to the spine.

15. The method of claim 13, wherein the portion is less than or equal to about one-quarter of the first intervertebral disc.

16. The method of claim 15, wherein the portion is located within less than or equal to an about ninety degree angular circumferential region of the first disc in a transverse plane relative to the spine.

17. The method of claim 1, further comprising imaging the labeled pain factor using an imaging tool that comprises a phosphor imaging plate.

18. The method of claim 1, further comprising:
using a local injection assembly to inject the targeted label into a third intervertebral disc in the spine of the patient and which comprises a third region of tissue at a third location;
binding the pain factor at the third location with the targeted label injected into the third disc, thereby artificially labeling the pain factor with the targeted label at the third location in a manner substantially increasing the ability to image the pain factor at the third location with the imaging tool; and
wherein imaging the labeled pain factor further comprises imaging the third intervertebral disc to thereby image a third concentration in the third region of tissue at the third location.

19. The method of claim 1, further comprising imaging the first and second locations of the targeted label bound to the pain factor in a manner that enhances the directed delivery of localized therapy to the location diagnosed as painful.

20. The method of claim 1, further comprising:
conducting a therapeutic procedure in a substantially localized manner to the location diagnosed as painful.

21. The method of claim 20, wherein the therapeutic procedure is adapted to substantially alleviate generation or transmission of pain at the painful location.

22. The method of claim 20, wherein the therapeutic procedure is adapted to substantially ablate at least one nerve at the painful location.

23. The method of claim 20, wherein the therapeutic procedure comprises delivering at least one therapeutic chemical in a substantially localized manner to the painful location.

24. The method of claim 20, wherein the therapeutic procedure comprises:
delivering a therapeutic dose of energy in a substantially localized manner to the painful location.

25. The method of claim 24, wherein delivering the therapeutic dose of energy in the substantially localized manner to the painful location further comprises:
ablating at least one nerve at the painful location with the therapeutic dose of energy.

26. The method of claim 24, wherein delivering the therapeutic dose of energy in the substantially localized manner to the painful location further comprises:
delivering ultrasound energy to the painful location.

27. The method of claim 26, wherein delivering the ultrasound energy further comprises:
delivering the ultrasound energy in a directed manner locally into the painful location from a delivery location.

28. The method of claim 27, wherein:
the delivery location is outside of the patient; and
the ultrasound energy is delivered via high intensity focused ultrasound (HIFU) that is adapted to focus the ultrasound energy to the painful location.

29. The method of claim 27, wherein:
the delivery location is adjacent to the painful location within the patient; and the ultrasound energy is delivered via a directional ultrasound probe.

30. The method of claim 24, wherein the therapeutic dose of energy comprises thermal energy.

31. The method of claim 30, wherein the therapeutic dose of energy further comprises electrical energy delivered via a radiofrequency (RF) probe.

\* \* \* \* \*